US008316653B2

(12) United States Patent
Appler et al.

(10) Patent No.: US 8,316,653 B2
(45) Date of Patent: Nov. 27, 2012

(54) INSPECTION PORT

(75) Inventors: Paul C. Appler, Windsor (CA); Jack E. Brass, Toronto (CA); Steven M. Knowles, North Manchester, IN (US); Donald L. Klipstein, Upper Darby, PA (US)

(73) Assignee: Brasscorp Limited, North York (CA)

( * ) Notice: Subject to any disclaimer, the term of this patent is extended or adjusted under 35 U.S.C. 154(b) by 1056 days.

(21) Appl. No.: 12/299,606

(22) PCT Filed: May 4, 2007

(86) PCT No.: PCT/CA2007/000803
§ 371 (c)(1),
(2), (4) Date: Nov. 4, 2008

(87) PCT Pub. No.: WO2007/128127
PCT Pub. Date: Nov. 15, 2007

(65) Prior Publication Data
US 2009/0183516 A1    Jul. 23, 2009

Related U.S. Application Data

(60) Provisional application No. 60/797,225, filed on May 4, 2006, provisional application No. 60/844,320, filed on Sep. 13, 2006, provisional application No. 60/844,539, filed on Sep. 14, 2006, provisional application No. 60/845,913, filed on Sep. 20, 2006.

(51) Int. Cl.
*F25B 45/00* (2006.01)
(52) U.S. Cl. ............................................. 62/77
(58) Field of Classification Search .............. 62/77, 128, 62/264
See application file for complete search history.

(56) References Cited

U.S. PATENT DOCUMENTS
4,746,178 A    5/1988 Canty et al.
(Continued)

FOREIGN PATENT DOCUMENTS
CA    1335416    5/1995
(Continued)

OTHER PUBLICATIONS

"The Digital Headstart for Refrigeration Engineers?", Brochure for "Testo 523, 556, 560: Precision and assurance with the New generation of digital refrigeration system analyzers", 12 pages, obtianed from www.testo.com website on or about Apr. 30, 2007.
International Search Report and Written Opinion, PCT/CA2007/000813 dated Sep. 4, 2007.

*Primary Examiner* — Melvin Jones
(74) *Attorney, Agent, or Firm* — Henry B. Ward, III; Moore & Van Allen PLLC

(57) ABSTRACT

A manifold gauge set has at least one sight glass window for viewing contents of a refrigeration system or an air conditioning system being serviced. The window may be non-planar to achieve an appearance that varies with the presence or absence of liquid. Such a non-planar window may be in the form of a dome, prism, or a fresnel lens. The gauge set may have a second light transmissive window to allow light to illuminate system contents being viewed. A light source may be provided to illuminate system contents being viewed. The light source may provide light through the same window that is used for viewing contents. A diffuser may be provided with a second window to achieve an illuminated background for viewing system contents. Similar configurations may be used in standalone sight glasses, vacuum pumps, and recovery machines.

24 Claims, 21 Drawing Sheets

U.S. PATENT DOCUMENTS

| | | |
|---|---|---|
| 5,558,124 A | 9/1996 | Randall |
| 6,564,613 B1 | 5/2003 | Speer |
| 6,782,184 B2 | 8/2004 | Canty et al. |
| 7,073,346 B2 * | 7/2006 | Ramachandran et al. ...... 62/292 |
| 2003/0131622 A1 | 7/2003 | Rakowski et al. |
| 2005/0092010 A1 * | 5/2005 | Ramachandran et al. ...... 62/292 |

FOREIGN PATENT DOCUMENTS

| | | |
|---|---|---|
| CA | 2211898 | 8/1996 |
| EP | 1197712 | 4/2002 |

* cited by examiner

INSPECTION PORT

CROSS-REFERENCE TO RELATED APPLICATIONS

This application claims priority from, and the benefit of, the filing date of U.S. Patent Application 60/797,225 filed 4 May 2006 under title Inspection Port, the filing date of U.S. Patent Application 60/844,320 filed 13 Sep. 2006 under title Inspection Port, the filing date of U.S. Patent Application 60/844,539 filed 14 Sep. 2006 under title Inspection Port, the filing date of U.S. Patent Application 60/845,913 filed 20 Sep. 2006 under title Inspection Port and the filing date of International Patent Application PCT/CA2007/000803 filed May 4, 2007 under the title Inspection Port. The contents of the above applications are hereby incorporated by reference into the Detailed Description hereof.

TECHNICAL FIELD

The invention relates to manifold gauges. More particularly the invention relates to manifold gauges with means to determine the presence of fluid in the manifold gauge, and the methods related thereto.

BACKGROUND ART

In this description reference will be made to refrigeration systems. An air conditioning system is a form of refrigeration system. Accordingly, the term refrigeration system will be used herein; however, it is to be understood that any reference to a refrigeration system herein includes an air conditioning system.

During service of refrigeration systems it is common practice to use devices in fluid connection with the refrigeration system, such as for example a pressure gauge set. Such a gauge set is sometimes referred to as a manifold gauge set and that term will be used in this description. The manifold gauge set allows the service technician to connect hoses to the high pressure and low pressure sides of the a/c or refrigeration system, as well as to a bottle of refrigerant or other refrigerant source, as well as to a vacuum pump or other devices. The technician can then observe the pressures, put refrigerant into the system, remove refrigerant from the system, pull a vacuum on the system and in general access the system for service.

The gauge set typically has a sight glass built into the body of the gauge set. This sight glass is a piece of transparent glass or plastic through which the technician can observe a stream of refrigerant as it passes through the gauge set.

As an example, during service a stream of refrigerant and can be observed to see any bubbles in the liquid stream and to see the condition (color) of the refrigerant and oil since these visible conditions can indicate impurities in the refrigerant and/or in the lubricant.

Any bubbles indicate that service may not be complete. The technician can continue to add refrigerant into the system and observe the liquid stream until all bubbles are gone, then the system is charged correctly. Any discoloration seen in the refrigerant or lubricant can indicate impurities in the refrigerant or in the lubricant.

The technician should also observe to see if the gauge set body cavity is full of liquid (no bubbles) or completely empty.

Improvements or alternatives to current devices and methods utilized for fluid connection with refrigeration systems are desireable.

DISCLOSURE OF THE INVENTION

In a first aspect the invention provides a device for use in servicing a refrigeration system. The device includes a body having a cavity and a viewing window for viewing contents of the cavity. The device also includes a first hose connection port in fluid communication with the cavity and a second hose connection port in fluid communication with the cavity. The hose connection ports are for forming respective fluid connections as part of a conduit in fluid connection with the refrigeration system. The device also includes a path through the body outside the hose connection ports. The path is for allowing illumination of the cavity. The device also includes a light source illuminating the cavity through the path with the light source mounted to the device.

The path may include an aperture through the body outside the viewing window and a light transmissive window enclosing the aperture. The viewing window and the light transmissive window may oppose one another across the cavity such that the cavity is backlit for the viewing window by light through the light transmissive window. The light transmissive window may include a diffuser for diffusing light from the light source before the light enters the cavity.

The device may include a third hose connection port in fluid communication with the cavity. The third hose connection port is also for forming a fluid connection as part of the conduit in fluid connection with the refrigeration system. The device may also include a first valve and a second valve. The first valve is for controlling fluid communication between the first hose connection port and the third hose connection port through the cavity, while the second valve is for controlling fluid communication between the second hose connection port and the third hose connection port.

The device may include a first pressure gauge and a second pressure gauge. The first pressure gauge is for measuring and displaying pressure in the cavity at the first hose connection port. The second pressure gauge is for measuring and displaying pressure in the cavity at the second hose connection port.

The device may be a manifold gauge set. The device may be a refrigerant recovery machine for drawing refrigerant through the cavity from the first hose connection port to the second hose connection port. The device may be a vacuum pump for drawing a vacuum through the cavity from the first hose connection port to the second hose connection port.

The viewing window may include a magnification lens for magnifying the contents of the cavity. The device may include a liquid presence indicator for indicating the presence of liquid in the cavity.

The liquid presence indicator may be visible through the viewing window. The liquid presence indicator may be within the viewing window. The liquid presence indicator may include a lens altering the appearance of the contents of the cavity through the viewing window when liquid is present in the cavity as compared to when liquid is absent from the cavity. The device may include a lens that magnifies the contents of the cavity when liquid is present in the cavity.

The device may be an inline sight glass. The light transmissive window may be transparent and colorless. The light transmissive window may allow light external to the device to illuminate the cavity for the viewing window.

The light source may include at least one LED. The light source may include a plurality of LEDs. At least one LED may emit white light and at least one LED different from the white LED may emit light for causing visible fluorescence of fluids utilized in refrigeration systems.

The device may include control circuitry for activating the at least one LED for white light independently from the at least one LED for causing visible fluorescence.

The light source may be mounted to the body to provide illumination of the cavity through the light transmissive window.

The viewing window may be non-planar such that liquid in the cavity in contact with the viewing window appears different when viewed from the viewing window as compared to the appearance of the cavity when liquid is absent from the cavity. The non-planar viewing window may be in the form of a dome. The viewing window and light transmissive window may be integrated together in the form of a tube. The non-planar viewing window may be in the form of a fresnel lens whose ridges would be in contact with liquid if liquid is present.

The light source may be removable.

The light source may include a housing and connections for a battery to power the light source. The light source may accept power from an external power source to power the light source. The light source may include means to automatically prevent power from being consumed from the battery when external power is being provided.

In a second aspect the invention provides a method of servicing a refrigeration system. The method includes forming respective fluid connections to a first hose connection port and to a second hose connection port as part of a conduit for fluid connection with the refrigeration system. The hose connection ports are part of a device having a body and the hose connection ports are in fluid communication with a cavity of the body. The body has a viewing window for viewing contents of the cavity and the body has a path through the body outside the hose connection ports. The viewing window is for viewing of the cavity. The method further includes illuminating the cavity through the path and viewing the cavity through the viewing window while the path is illuminated and contents from the refrigeration system are flowing through the cavity.

The method may include opening at least one valve between the hose connection ports to allow fluid in the conduit to flow between the first hose connection port and the second hose connection port through the cavity while the cavity is illuminated and the cavity is being viewed through the viewing window.

The method may include forming a fluid connection to a third hose connection port as part of the conduit for fluid connection with the refrigeration system. The method may include opening at least one valve between the first and third hose connection port to allow fluid in the conduit to flow between the first hose connection port and the third hose connection port through the cavity while the cavity is illuminated and the cavity is being viewed through the viewing window. The method may include opening at least one valve between the second and third hose connection port to allow fluid in the conduit to flow between the second hose connection port and the third hose connection port through the cavity while the cavity is illuminated and the cavity is being viewed through the viewing window.

Illuminating the cavity may include diffusing light from the light source before the light illuminates the cavity. Illuminating the cavity may include illuminating the cavity from opposite the viewing window such that the cavity is backlit with respect to the viewing window.

In a third aspect the invention also provides a manifold gauge set for use in servicing a refrigeration system. The manifold gauge set includes a body having a cavity and a viewing window for viewing contents of the cavity. The manifold gauge set includes at least three hose connection ports in fluid communication with the cavity. The manifold gauge set includes at least two valves. The valves for controlling fluid communication between the hose connection ports and the cavity. The manifold gauges set further includes two pressure gauges, one gauge associated with one of the hose connection ports and another gauge associated with another one of the hose connection ports, each gauge for reading and displaying the pressure at its associated hose connection port. The manifold gauge set further includes a path through the body outside the hose connection ports and the viewing window. The path is for allowing illumination of the cavity.

The path may include a light transmissive window through the body to the cavity. The light transmissive window may include an aperture through the body to the cavity and a transparent lens sealed about the aperture. The light transmissive window may oppose the viewing window across the cavity such that the cavity is backlit for the viewing window by light through the light transmissive window.

In a fourth aspect the invention provides a manifold gauge set for use in servicing a refrigeration system. The manifold gauge set includes a body having a cavity, at least three hose connection ports, each post in fluid communication with the cavity, and at least two valves for controlling fluid communication between the ports and the cavity, at least one valve being a multi-position rotational valve allowing control over the flow of fluid through the cavity by rotation of a handle of the valve, and two pressure gauge, one gauge associated with one of the hose connection ports and another gauge associated with another one of the hose connection ports, each gauge for reading and displaying the pressure at its associated hose connection port, and a ring associated the handle of each multi-position valve, the ring comprising position indicators to indicate rotational position of the handle.

The position indicators may include numbers equally spaced about the ring to indicate rotational position. The ring may be setably fixed to the handle such that the calibration ring can be moved with respect to the handle to set the calibration ring at a desired position indicator for a selected position of the handle.

In a fifth aspect the invention provides a manifold gauge set for use in servicing a refrigeration system. The manifold gauge set includes a body having a cavity, at least three hose connection ports, each post in fluid communication with the cavity, and at least two valves for controlling fluid communication between the ports and the cavity, at least one valve being a multi-position rotational valve allowing control over the flow of fluid through the cavity by rotation of a handle of the valve, and two pressure gauge, one gauge associated with one of the hose connection ports and another gauge associated with another one of the hose connection ports, each gauge for reading and displaying the pressure at its associated hose connection port, and a liquid presence indicator for indicating the presence of liquid in the cavity.

Other aspects of the present invention and additional or alternative elements of the above aspects, including for example methods of use, will be evident from the further description and the drawings herein.

BRIEF DESCRIPTION OF THE DRAWINGS

For a better understanding of the present invention and to show more were clearly how it may be carried into effect, reference will now be made, by way of example, to the accompanying drawings which show the preferred embodiment of the present invention and in which.

MODES FOR CARRYING OUT THE INVENTION

Figure 1:
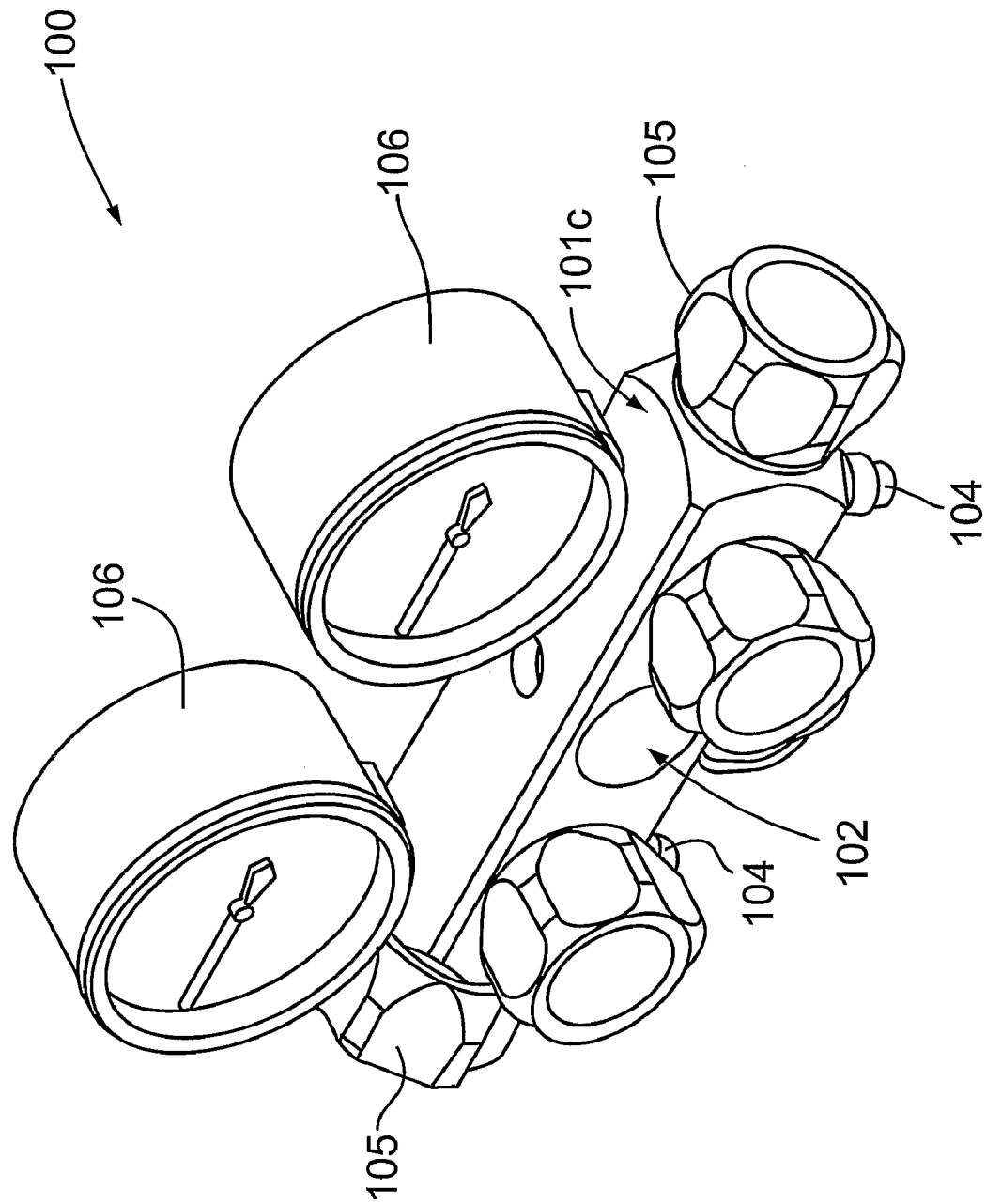
FIG. 1 is a front perspective view of an example embodiment of a manifold gauge set.

Throughout this description like reference numerals will be used to identify similar elements from embodiment to embodiment unless specifically indicated otherwise the description for like elements having like reference numeral-sapplies equally to such elements and will not be repeated from the description of one embodiment to the next.

Figure 2:
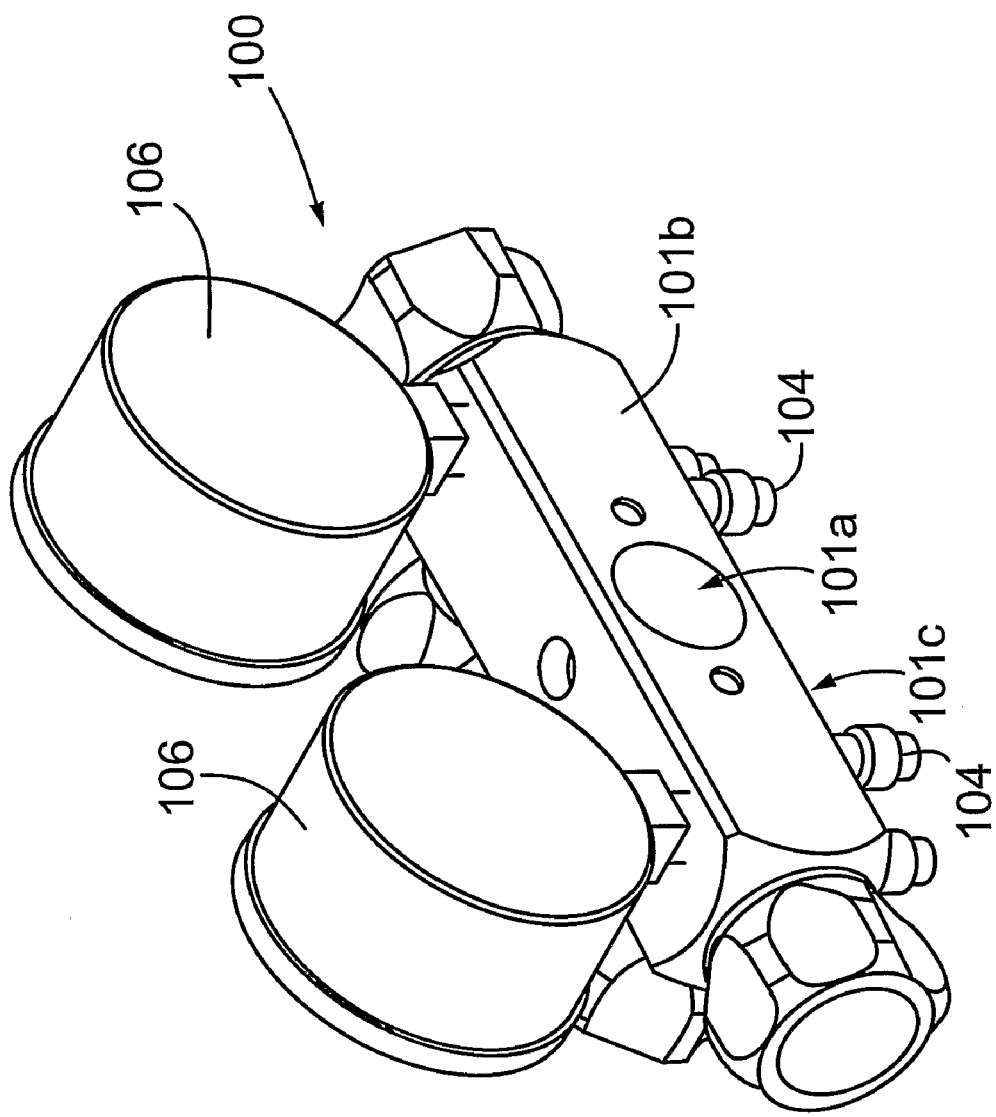
FIG. 2 is a rear perspective view of the embodiment of FIG. 1.

Referring to FIGS. 1 and 2, a gauge set 100 having a second sight glass window 101a on rear 101b of gauge set body 101c directly inline with front sight glass window 102, such that there is a through bore all the way through gauge set body cavity (see for example body cavity 103 in FIG. 4) where the liquid stream flows.

This allows ambient light to enter the gauge set 100 through the window 102 and exit through the window 101a. It also allows ambient light to enter through the window 101a and exit out the front sight glass 102. This description will primarily be made with respect to viewing of the cavity 103 through the front sight glass window and illumination through the rear sight glass window 101a; although, it is recognized that the viewing may be reversed in some embodiments.

Accordingly, the window 102 will be considering as a viewing window 102, while the window 101a is a path through the body 101c for allowing illumination of the cavity 103. The window 101a is a light transmissive window 101a through the body to the cavity 103. It is recognized that the viewing window is also light transmissive; however, the viewing window must be transparent such that the technician can see the contents of the cavity 103. The light transmissive window 101a need not be transparent in order to perform cavity illumination.

In either case, the liquid stream flowing through a body cavity (provided between the front sight glass 102 and the rear sight glass 101a) is illuminated with ambient light making any bubbles in the stream and the condition (as indicated typically by color) of the refrigerant much easier to see. A technician could also place a light source behind the gauge set 100 to provide even more light shining through the windows 101a, 102, which will illuminate the bubbles even more and make it even easier to observe the condition (color) of the refrigerant and oil and other stream contents.

The window 101a may be in the form of or substituted with a piece of translucent material, such as ground glass or a suitable translucent piece of plastic which will act as a diffuser. Any transparent window 101a may be accompanied by a diffuser. Such a diffuser may improve the illumination distribution within the body cavity 103 or improve the visibility of irregularities in liquid within the body cavity 103 by providing an illuminated background to see such irregularities against.

Hose connection ports 104 are provided with fluid connection to the cavity 103. The liquid stream through the cavity 103 between the ports 104 is controlled by control valves 105. Pressure at the ports 104 is measured and displayed by pressure gauges 106. The ports 104 are used to form fluid connection to hoses, not shown, in a manner known in the art. The cavity 103 and hoses form a conduit for further fluid connection to a refrigeration system in a manner known in the art, and to a charging station, a vacuum pump, a refrigerant recovery machine, or a refrigerant recycling and recovery machine, not shown, in a manner known in the art. The manifold gauge set 100 has four valve 105 and four ports 104. The manifold gauge set 100 valves and ports operate can operate in a manner similar to exits four valve gauge sets.

The hose connection ports 104 may provide manually releasable fluid connections. For example, the ports 104 shown in the FIGS. are quick disconnect fittings typically used in association with R134A refrigerant applications. Other fittings, such as for example, manually releasable threaded fittings typically used in association with R12 refrigerant applications, may be used. Non-manually releasable fittings such as threaded connection tightened by tools, such as a wrench, may also be used where it is desired to attach hoses to the manifold 100 for long term use.

Figure 3:
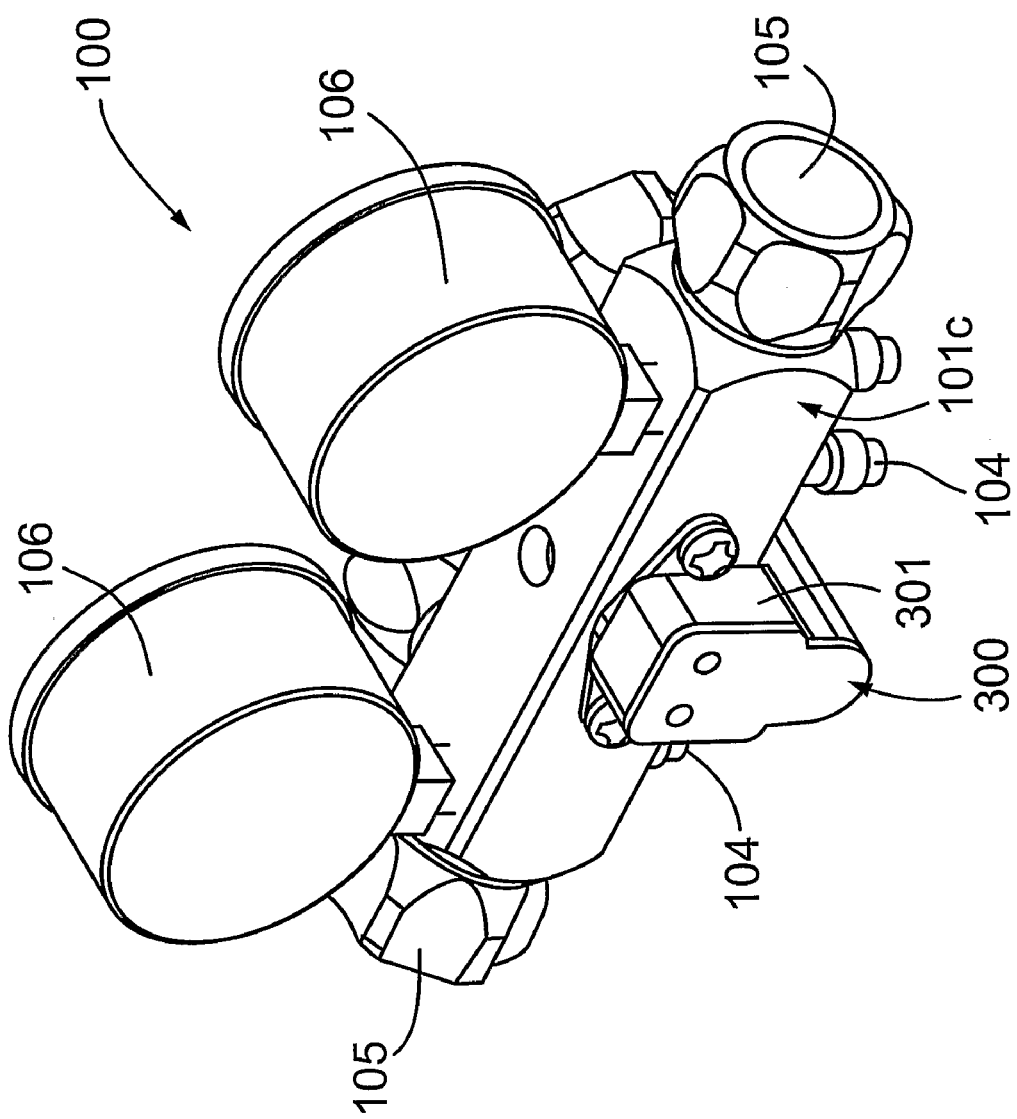
FIG. 3 is a rear perspective view of another example embodiment of an aspect of the present invention.

Referring to FIG. 3, a light source 300 is provided on the body 101c of the gauge set 100 which provides a light to shine through the window 101a. An LED type light bulb or any type of light source is mounted in a housing 301 on the rear 101b of gauge set 100 such that a light shines into the window 101a providing light to the interior body cavity 103 and illuminating, for example, the bubbles in the liquid stream. This light source 300 can be in a housing 301 or just an open light source. As shown, the light source 300 can be mounted, by screws or the like, on the rear 101b of the body 101a to shine through the window 101a (not visible in FIG. 1 or 3). As an example alternative light source 300 can be mounted on the front of the housing 301 to shine through the window 102 (not visible in FIG. 2 or 3), or it could be in the interior of the body 101c itself illuminating the cavity 103 directly. The light source 300 could also be mounted to the device at another location inside or outside the gauge body 101c and aimed to illuminate the interior body cavity 103. The light source 300 may be located anywhere as long as it provides illumination into the body cavity. Consequent modification of the light source 300 may be required for the particular configuration chosen.

Variations of this embodiment include for example fiber optic means directing light into the body cavity 103 through an alternate path through body 101b or either window 101a, 102 from an LED or other light producing element in the light source 300. This can permit alternative mounting arrangements of the light source 300.

In a variation of this example embodiment, the light source 300 provided can be a UV (ultraviolet) light source. A UV light source is often used to detect the presence of ultraviolet reacting dyes that are placed in refrigeration systems to detect leaks. By observing the liquid stream with a UV light source it is possible to detect this dye in the refrigeration system. A filter, not shown, can be used at the viewing window 102 to avoid harmful emissions reaching the viewer.

Further variations of this embodiment can for example have a visible fluorescence-causing light source produce visible violet light or blue light in addition to or in lieu of ultraviolet light. For example, light sources that produce wavelengths that are used in inspection lamps to detect refrigerant leaks can be utilized in the light source 300. For example, LED inspection lamps used to detect refrigerant leaks can have UV or violet LEDs having a peak wavelength in the range of 390 to 410 nm. Other LED inspection lamps used to detect refrigerant leaks have one or more LEDs with peak wavelength anywhere from 440 to 475 nm. Accordingly, sources of light of such wavelengths can be used. Any wavelength in the range of 340 to 480 nm may be found useful for causing fluorescence of fluorescent dyes added to lubricants for mixing with refrigerants.

The light source 300 can have one or more LEDs or any combination of LEDs producing wavelengths suitable for causing fluorescence. The light source 300 may have a fluorescence-causing LED or combination of fluorescence-causing LEDs with one or more visible LEDs such as a white LED in addition.

Figure 4:
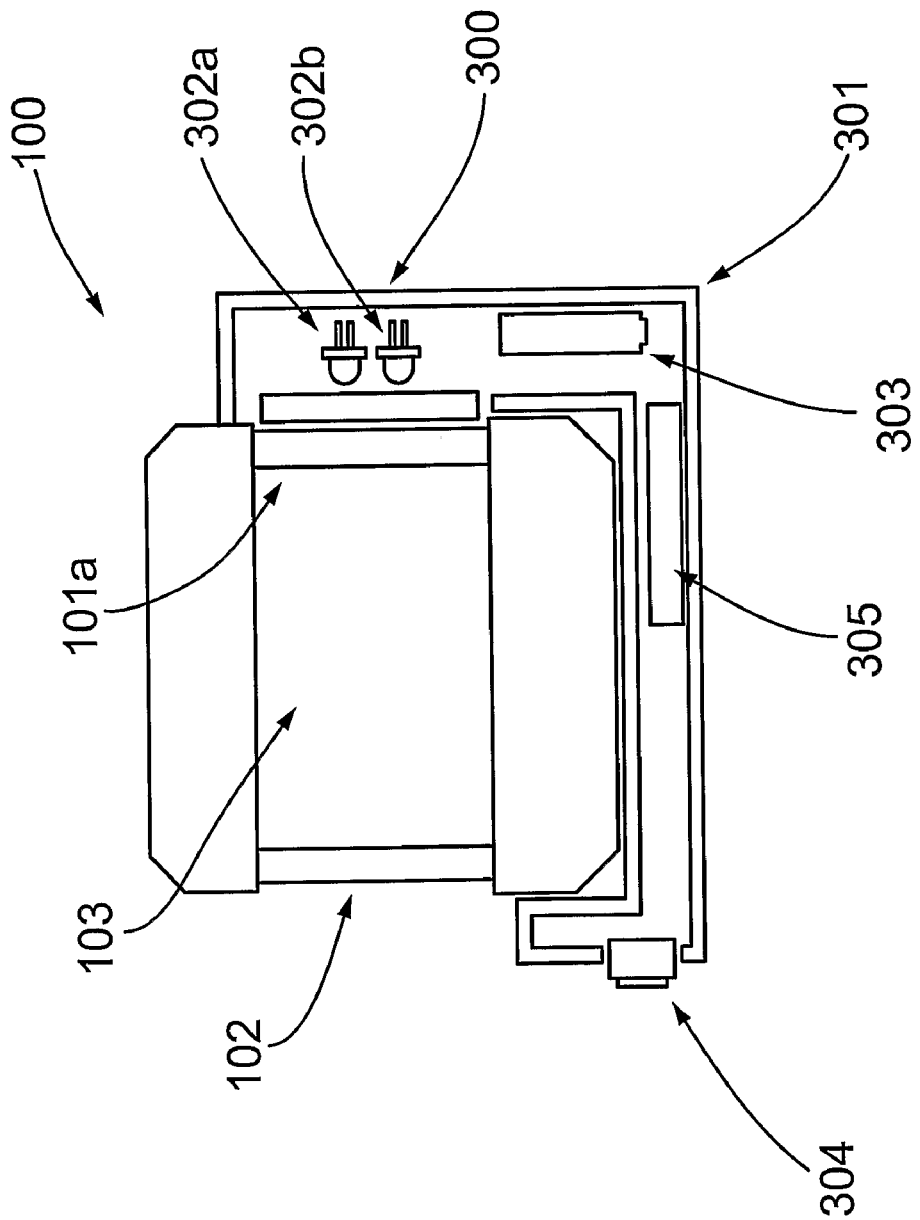
FIG. 4 is a cross sectional side view of the embodiment of FIG. 3.

Referring to FIG. 4, a cross section of the gauge set 100 and the light source 300 shows greater detail. Both the window 101a and the window 102 are shown, as well as the body cavity 103. A white LED 302a and a UV LED 302b are shown within the housing 301 of the light source 300. Also shown is a diffuser 303 provided between the LEDs 302a, 302b and the window 101a. The diffuser 303 is provided to provide an evenly illuminated background behind the window 101a so that bubbles, particles and other irregularities in liquid in the body cavity 103 are easier to see.

The diffuser 303 may be in the form of a translucent object such as a piece of translucent plastic. Alternatively, the diffuser 303 may be a piece of transparent sheet or plate material with one or both surfaces roughened, such as a piece of ground or etched glass. Further alternatively, the diffuser 303 may comprise one or two sheets of diffuser "filter gel" of a type available from performing arts theater supply shops. Other means can be found of achieving a diffuser 303.

A diffuser 303 having two distinct diffusing surfaces separated by the maximum allowable thickness of the diffuser 303 may provide more even distribution of light than is achievable with a piece of translucent plastic. Most translucent plastics also have a disadvantage of scattering different wavelengths of visible light unequally and that can result in the illuminated background achieved by the diffuser 303 having uneven color.

Alternative arrangements are possible, such as for example having LEDs 302a, 302b or other light sources directing light into an edge of the diffuser 303. The diffuser 303 may have light piping properties that are utilized for even distribution of light exiting its diffusing surfaces. Further alternatively for example, an electroluminescent backlight may be provided behind the window 101a, with or without a diffuser 303 or any UV LEDs 302b. Possible alternative light producing elements include miniature cold cathode fluorescent lamps.

Shown as provided are a battery 304a, switch 304b, and circuitry 305. For simplicity, electrical connections, such as for example wires and battery contacts between the battery 304a, switch 304b and circuitry 305, are not shown. The battery 304a, switch 304b, and circuitry 305 may be located in locations other than as shown.

The switch 304b is preferably a momentary contact pushbutton switch although or switches can be used. The circuitry 305 preferably includes a toggling circuit or a counter circuit so that the LEDs 302a, 302b can be switched on and off by repeatedly pressing the momentary contact pushbutton 304b. Alternatively, a pushbutton 304b may be a push-on-push-off type to negate the need for toggling or counter circuitry. If both at least one white LED 302a and at least one fluorescence-causing LED 302b are provided, then it is preferred to have means to switch these different LEDs 302a, 302b separately. This is preferably done by having the switch 304 being a momentary contact pushbutton and the circuitry 305 having a counter circuit to alternatively energize the white LED 302a, the fluorescence-causing LED 302b, or have all LEDs not energized. See, for example, the circuitry described with regard to FIG. 23. Alternatively, separate switches may be provided for the different LEDs 302a, 302b.

The battery 304a may be mounted inside or outside the housing 301 of the light source 300. The battery may be disposable or rechargeable. Any rechargeable battery 304a may be nickel cadmium, nickel metal hydride, lithium ion, or of an alternative chemistry such as lead acid. Charging circuitry may be provided in the light source housing 301 possibly incorporated in the circuitry 305. One or more solar cells may be provided for charging of any rechargeable battery.

A light source 300 having a battery 304a may also have means to accept power from an external power source, not shown, for the light producing elements. Such a variation of the light source 300 may have both a battery 304a and a power jack, not shown. Switching means such as diodes may be provided to prevent discharge of the battery 304a when external power is available. Charging circuitry may be provided to recharge any rechargeable battery 304a used with the light source 300 when external power is available.

The light source 300 may have a timer means such as a timer circuit incorporated in the circuitry 305 to automatically switch off the LED(s) or any other light producing element(s) to reduce wear of the battery 304*a* or any light producing elements.

Figure 5:
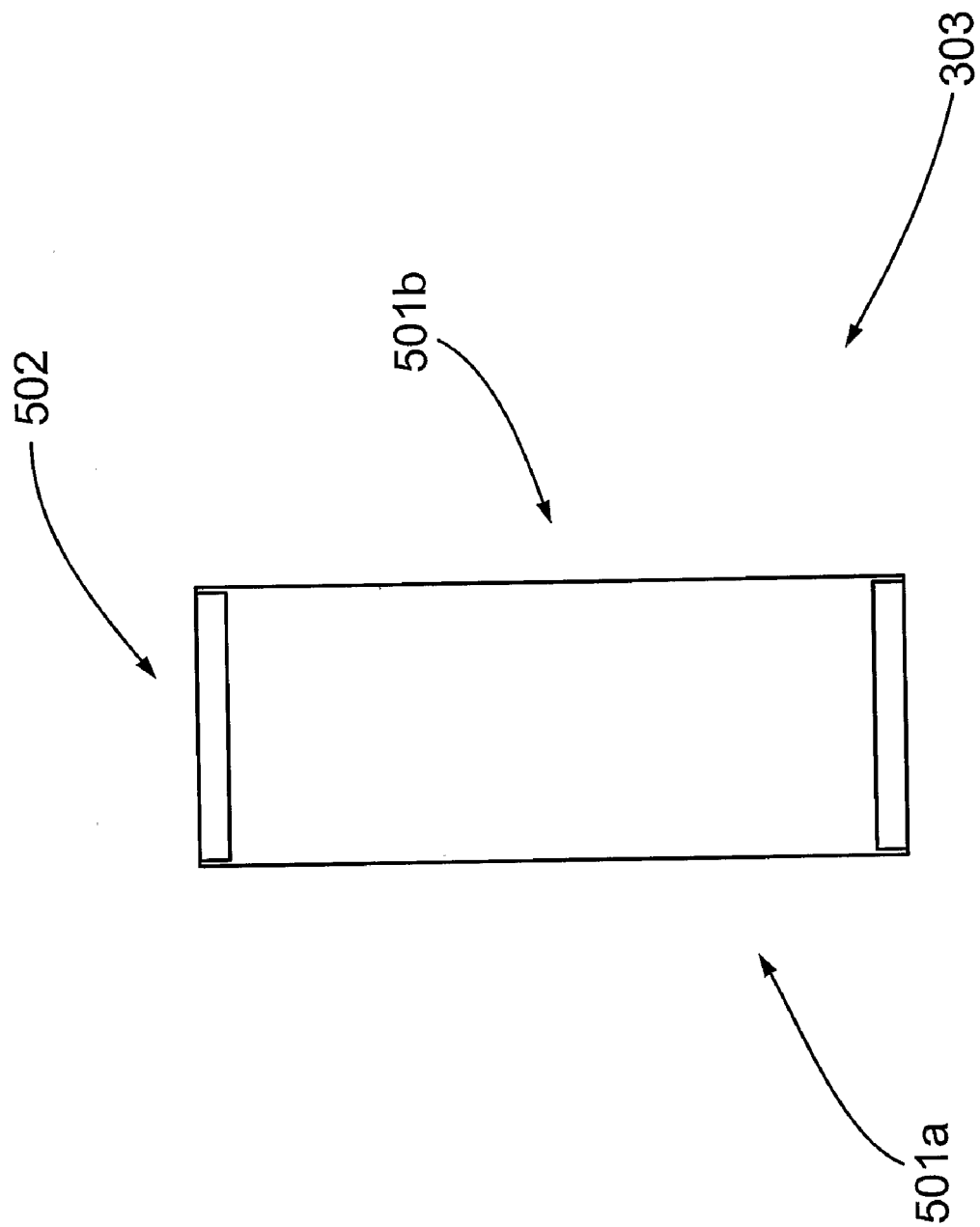
FIG. 5 is a cross section of a diffuser for use in the embodiment of FIG. 3.

Referring to FIG. 5, diffuser 303 may, for example, comprise two thin sheets of translucent material 501*a*, 501*b* and a short tube 502 that the translucent sheets are attached to. The tube 502 preferably has a white interior surface to assist even scattering of light onto the inside surface of the forward translucent sheet 501*a*. The translucent sheets 501*a*, 501*b* may be made of GAM 1075 or GAM 1080 or similar "diffusion filter gel". The two translucent sheets 501*a*, 501*b* are not necessarily identical.

Figure 6:
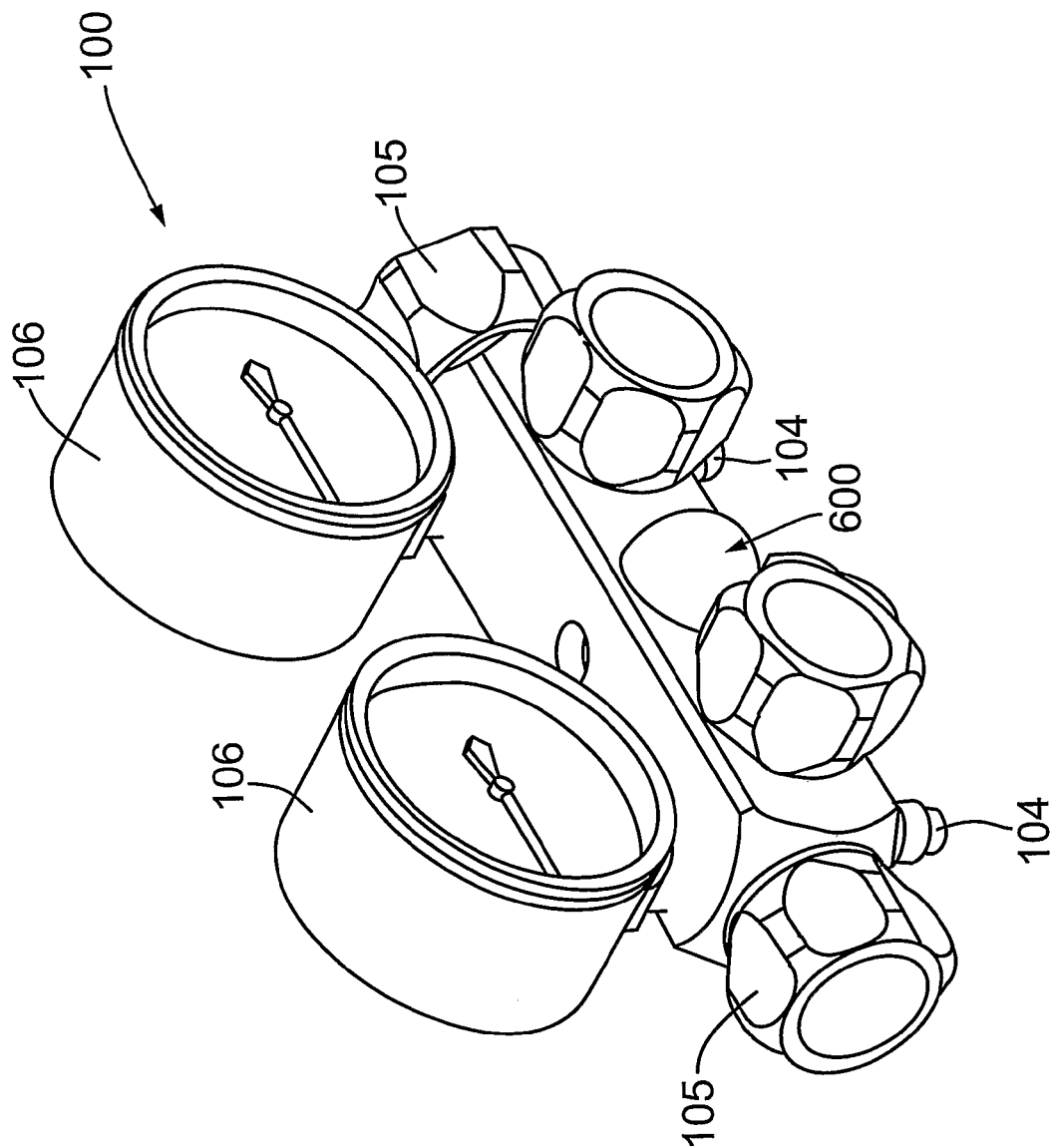
FIG. 6 is a front view of a further example embodiment of a manifold gauge set.
Figure 7:
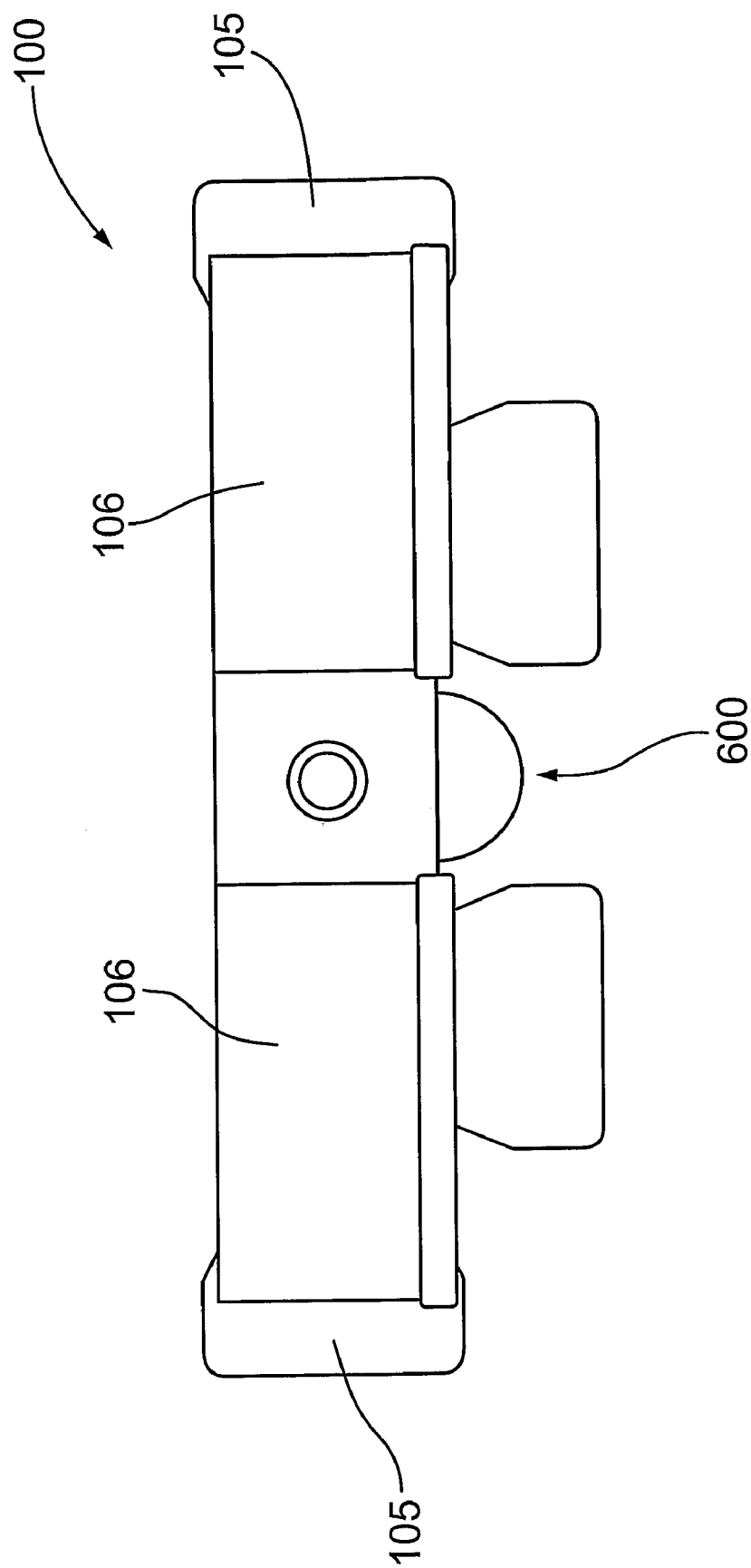
FIG. 7 is a top view of the embodiment of FIG. 6.

Referring to FIGS. 6 and 7, window 600 (which may be glass or clear plastic) is dome shaped such that it extends outward to gather more light and direct this added light into the body cavity 103. One or both of the sight glasses may be dome shaped if two windows 101*a*, 102 are provided. This dome shape also expands the angle at which one can observe the body cavity 103. This outward extension of the window gathers light and directs it into the body cavity 103. It also allows the viewer to be off to the side and still observe into the cavity 103. The dome may be shaped such that when filled with liquid the vision is directed in a direction different than if filled with gas such that this can indicate liquid or gas.

An advantage of a dome shaped window is that it allows the user to determine if the body cavity 103 is completely full of liquid or completely empty and/or if refrigerant is flowing through the cavity 103.

Various embodiments may have other means to determine whether or not the body cavity is filled with liquid.

The window may be shaped to magnify the image that is seen through the window. This may be accomplished with the dome shape glass mentioned above or by the glass being a special lens shape. A dome can magnify when filled with liquid and not magnify when filled with gas, which can also indicate if there is liquid present in the system.

As an alternative to a dome shaped sight glass, the window can have a prismatic or other shape to achieve an appearance change from light to dark or dark to light or showing a different color when liquid is present in order to indicate when liquid is present. This prism or other shape window can be illuminated by ambient light or illuminated with a light source. Further alternatively, the window may be a fresnel lens or otherwise be an essentially flat piece having ridges or grooves on the surface that liquid contacts. Lack of flatness of the surface that liquid contacts will achieve an appearance that varies with presence or absence of liquid.

The presence or absence indicator may exploit different refractive indices of liquids (such as liquid refrigerant) and gasses (such as gaseous refrigerant or air) to change the appearance through the viewing window. A point of reference could be an opposing light transmissive window which may appear larger or smaller depending on the presence or absence of liquid.

Figure 8:
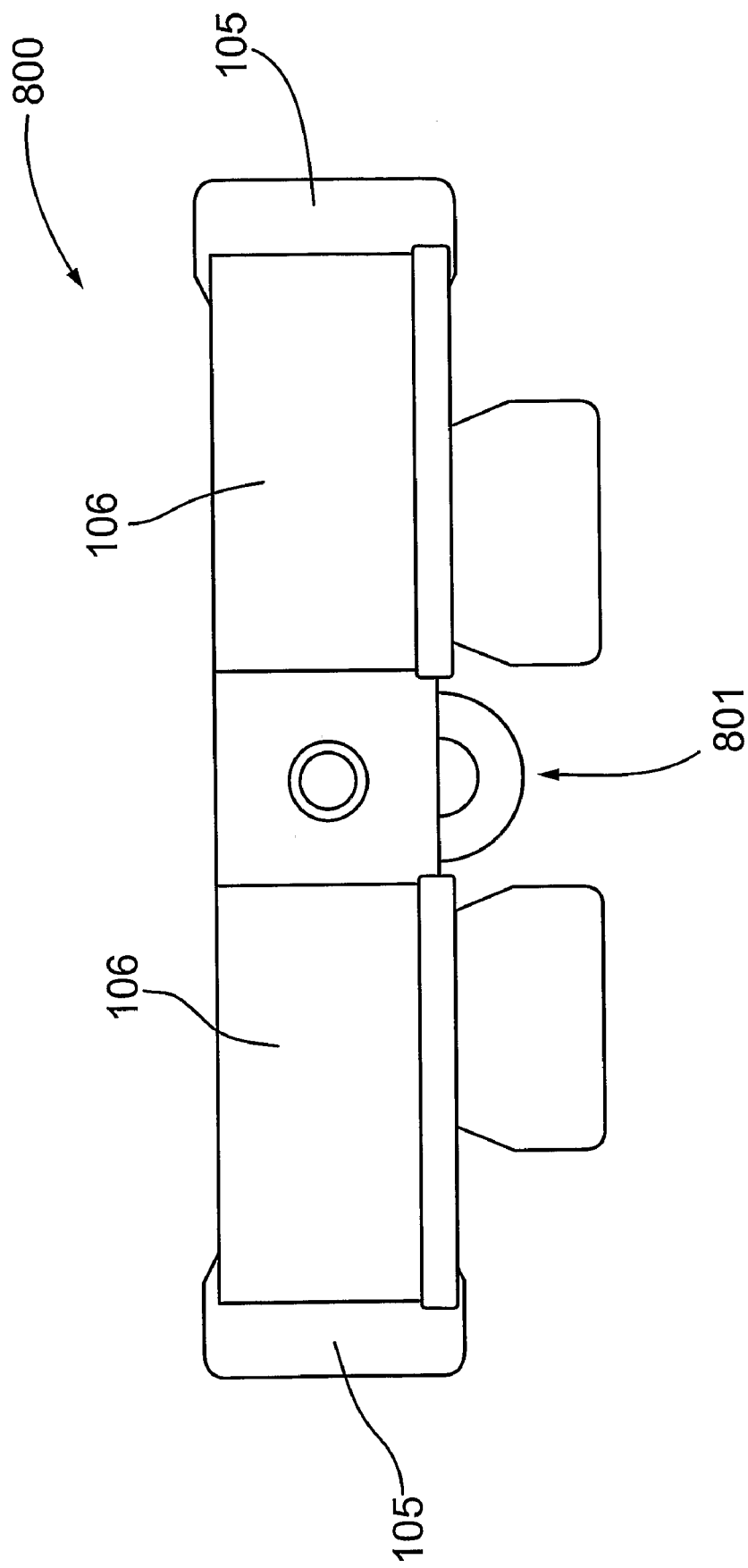
FIG. 8 is a front view of a still further example embodiment of a manifold gauge set.
Figure 9:
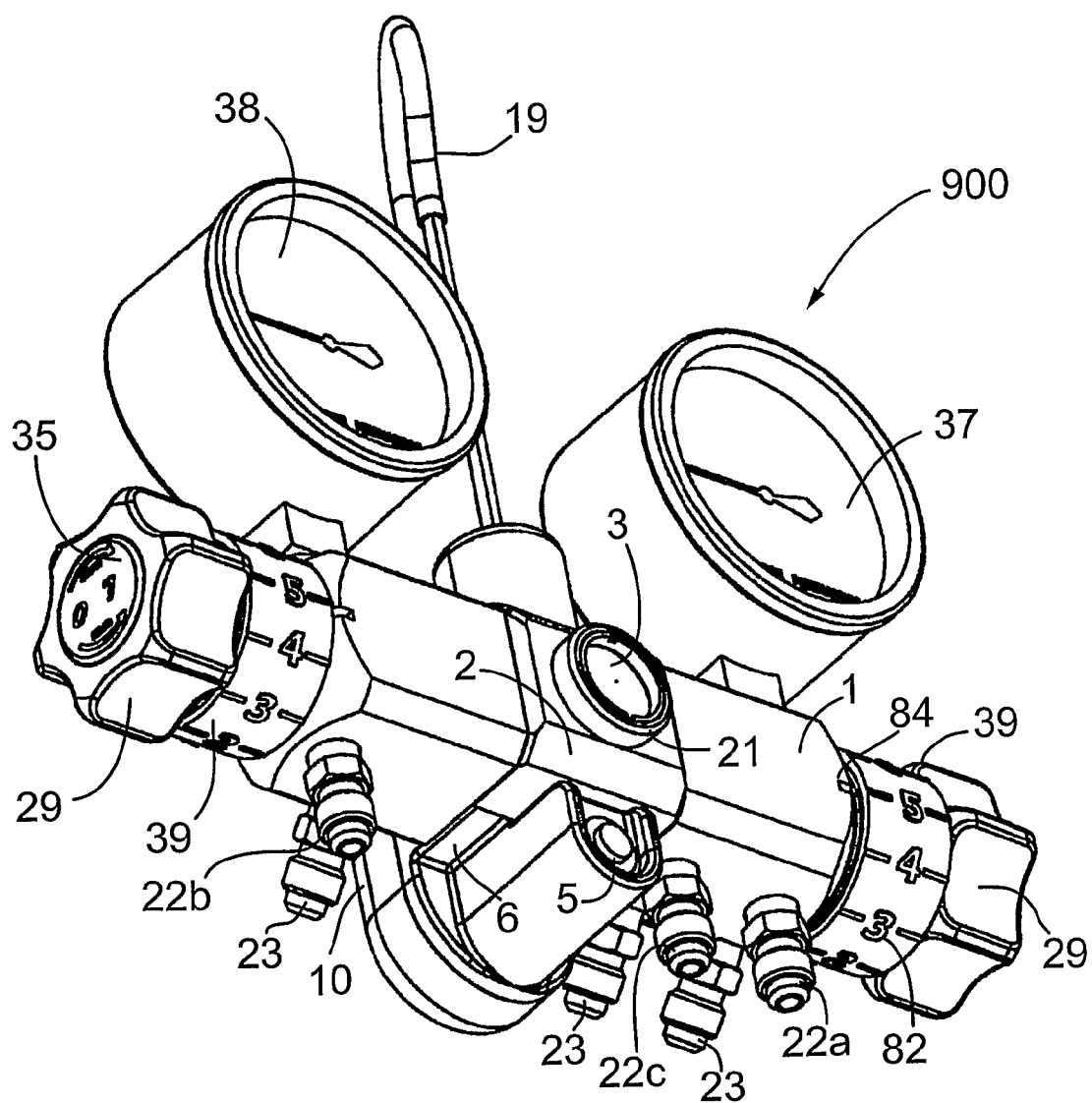
FIG. 9 is a perspective view from in front, below and to one side of alternative example embodiment of a manifold gauge set.
Figure 10:
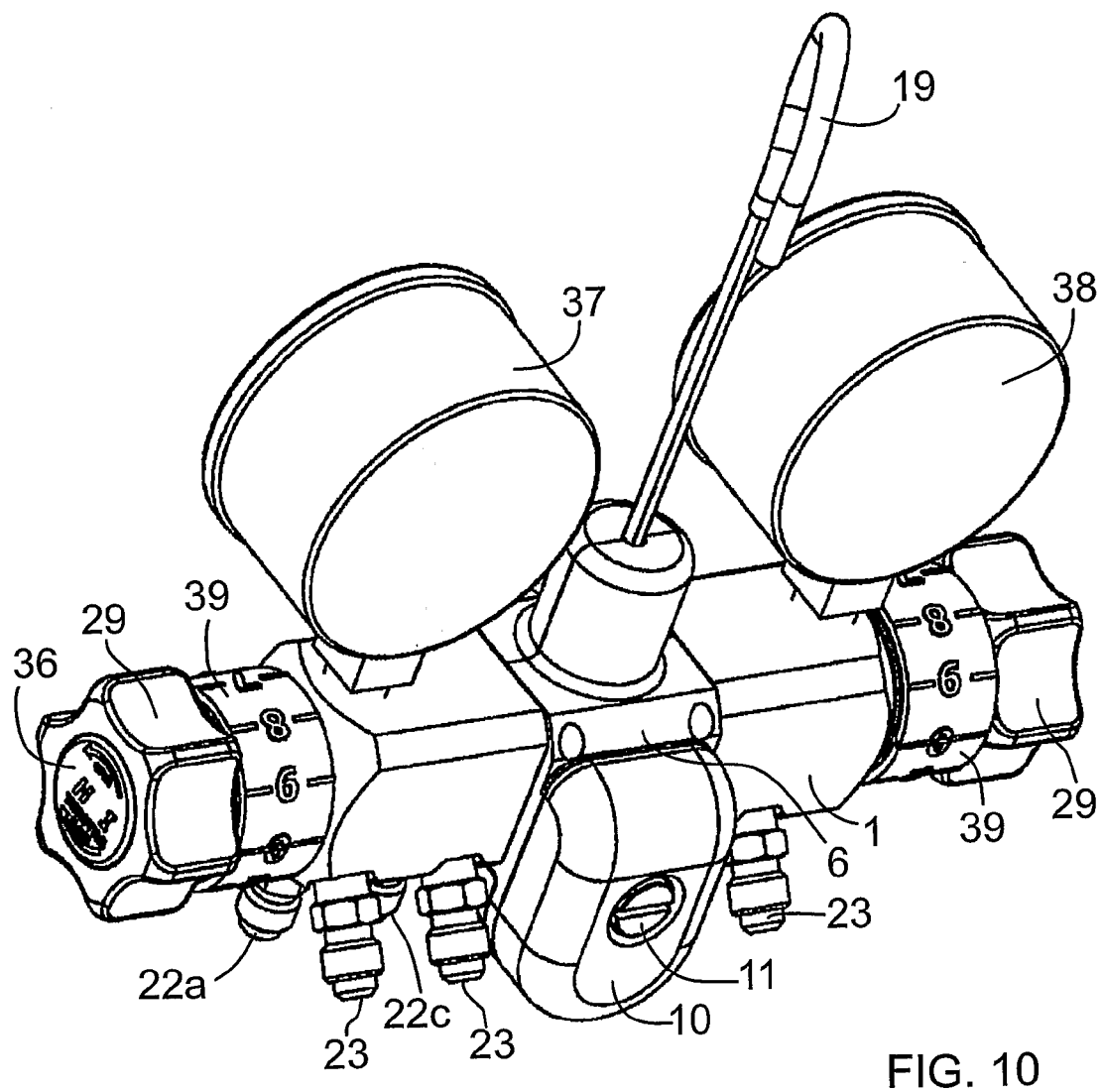
FIG. 10 is a perspective view from behind, above and to another side of the manifold gauge set of FIG. 9.
Figure 11:
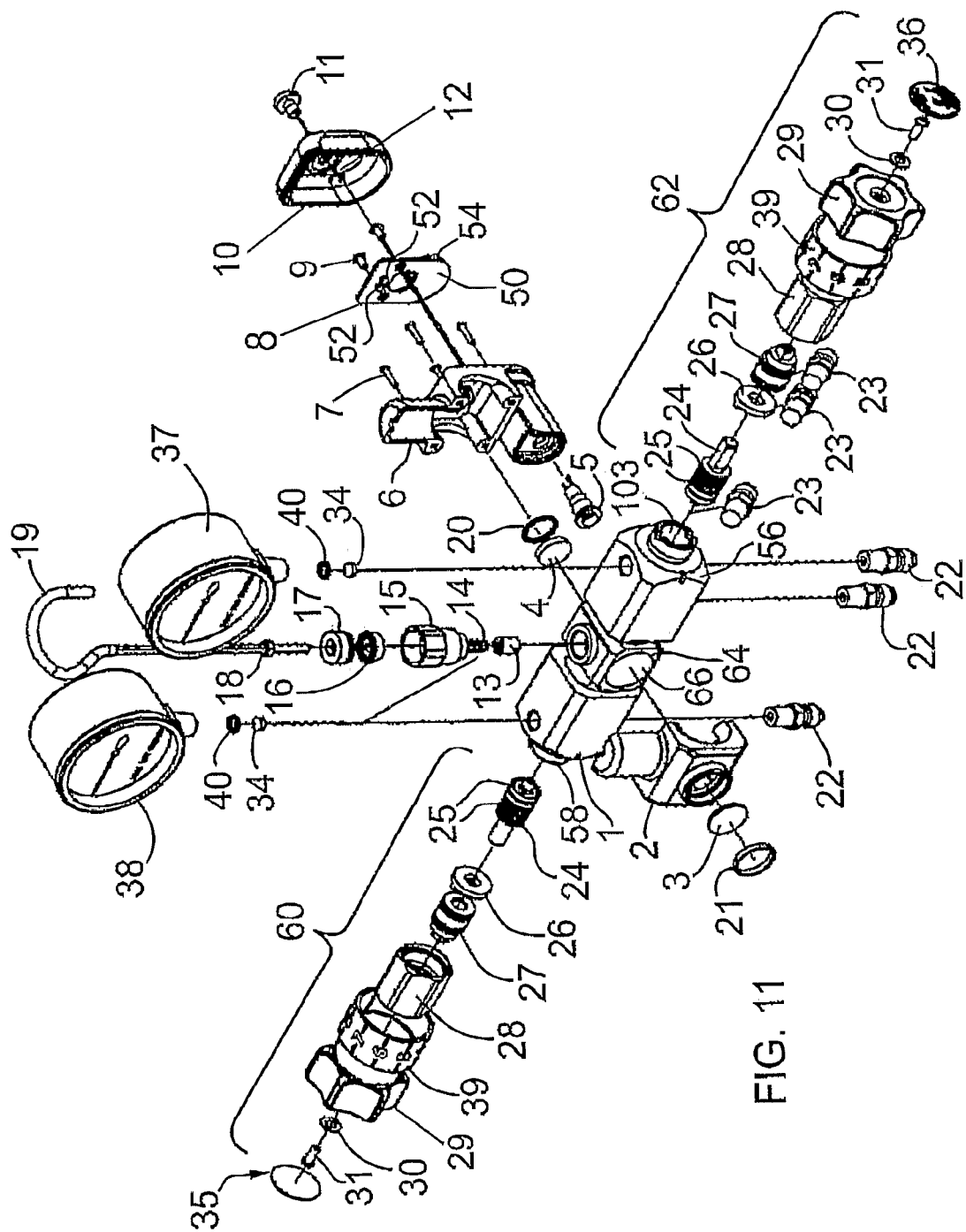
FIG. 11 is an exploded perspective view of the manifold gauge set of FIG. 9.
Figure 12:
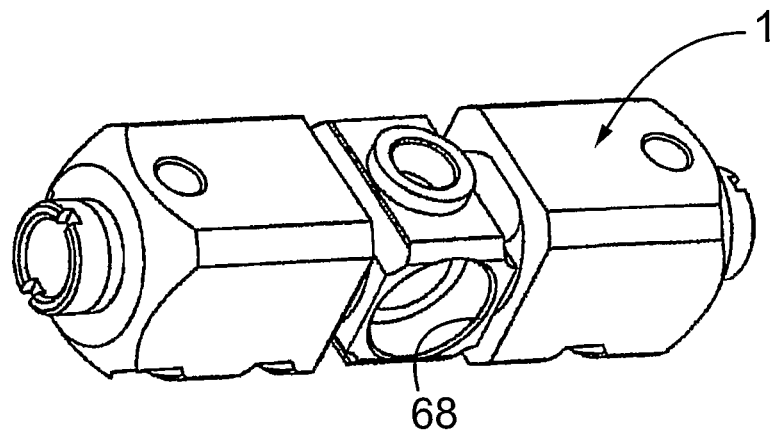
FIG. 12 is a rear perspective view of an example manifold body of use for example in the manifold gauge set of FIG. 9.
Figure 13:
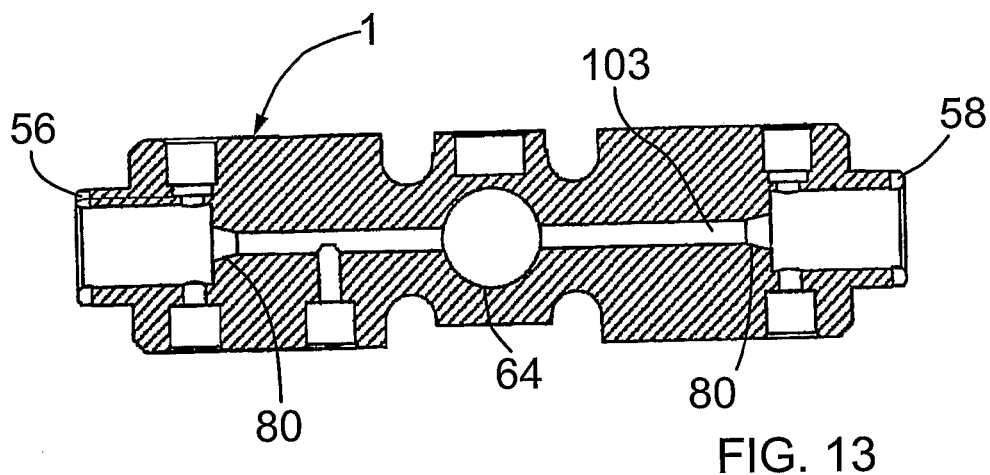
FIG. 13 is a rear cross-section view of the body of FIG. 12.
Figure 14:
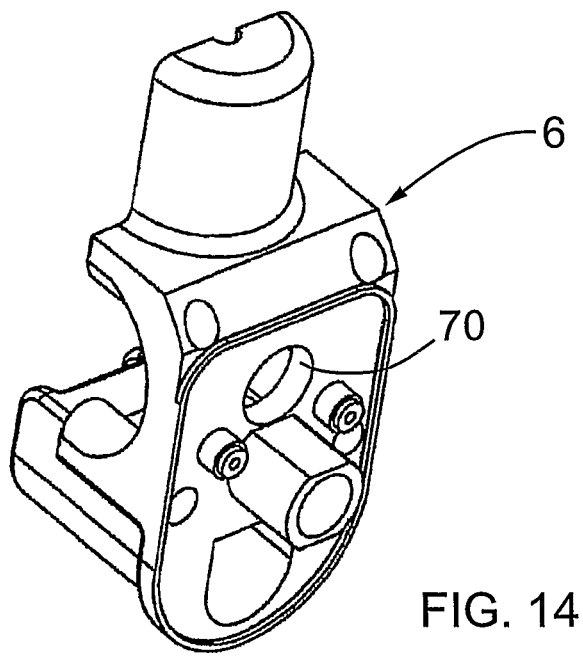
FIG. 14 is a rear perspective view of an example rear housing used for example on the manifold gauge set of FIG. 9.

Referring to FIG. 8, gauge set 800 has a window in the form of a tube 801. The tubular shape achieves an appearance that is different if the tube 801 is full of liquid as opposed to being free of liquid.

Other shapes and forms of the sight glass 801 can achieve an appearance that changes with presence or absence of liquid.

The gauge set 800 may have a light source 802 provided for illumination or causing fluorescence of fluids present in the window 801.

Means to indicate flow of fluid in order to make servicing of refrigeration systems easier and taking less time to complete. For example, a rotationally mounted fan wheel may be mounted within the body cavity 103 where the liquid stream will flow. The fan wheel is designed such that when liquid flows over it, it rotates. This rotation will indicate a the technician that there is flow within the body cavity 103 and its speed of rotation is an indication of how fast the flow is.

A float ball is used to indicate that there is liquid refrigerant in the cavity 103. The float ball is made of a material that will not float in a gaseous refrigerant but will float in a liquid refrigerant. Therefore, if the cavity 103 is full of gas, the ball will not float upward. When liquid is introduced into the cavity 103, the ball floats upward and indicates the level of liquid within the cavity 103.

The ball can be free floating within the cavity 103 or contained in a tube that runs inside the cavity 103, outside the cavity 103 or even outside the gauge set body 101*c*, the tube being exposed to the refrigerant flow such that it fills with liquid refrigerant when liquid is present. The float ball may visibly move if liquid is flowing. If liquid is flowing, the float ball may settle in a different position from the position that it settles in when liquid is not flowing.

Fan wheels or other means to indicate flow of liquids may also indicate flow of any gas or vapor that is present in lieu of a liquid. Preferably flow indication means are provided in combination with means of indicating presence or absence of liquid, such as a sight glass having a non-flat surface that liquid contacts.

Color can be an indicator of impurities in the refrigerant and/or oil. For example, the light from light source 300 which shines into the cavity 103 may be a certain frequency or color of light such that it indicates the condition of the refrigerant and oil by illuminating certain impurities in certain ways.

Any inspection port, including a viewing window combined with a light source or a viewing window combined with a light transmissive window to admit light, may be comprised in other devices, such as a vacuum pump or refrigerant recovery machine.

The terms front and rear have been used to distinguish between window 101*a* and window 102. For the purposes of this description the front window 102 is the window primarily used for viewing into the cavity 103. Ordinarily this would be viewable from in front of the manifold for ease of access by a technician; however, it could be on a top, rear or other position of the manifold gauge viewable by a technician. Window 101*a* may be used for secondary viewing of the cavity 103, or for illumination of the cavity 103 where viewable through the window 101*a*.

The window 101*a* could be opposite the window 102 as shown; however, it need not be in all embodiments. For example the window 102 could be viewable from in front of the manifold gauge 100 while the window 101*a* it is viewable from above. Where light is coming into the window 101*a* illuminates the cavity 103 such that an illuminated portion of the cavity 103 is viewable through the window 102.

Also, the light source 300 could be embedded in the manifold gauge such that the cavity 103 is illuminated for viewing through window 102 with or without providing window 101*a*. A path would be provided through the body 101*c* to allow light form the light source to illuminate the cavity 103 or to provide power to the light source to allow the light source to illuminate the cavity 103. A diffuser could be integrally formed with the light source, for example as part of the LED 302*a*, 302*b* package. Many other combinations to provide illumination of the cavity 103 based on the principles described herein are possible.

Referring to FIGS. 9-14, backlit illuminated manifold gauge set 900 has body 1, front housing 2, lens 3 providing magnification, retaining ring 21, diffuser 4, o-ring 20, switch 5, back housing 6, screws 7, light source 8, screws 9, back cover 10, screw 11, and retaining clip 12. The switch 5 is electrically connected to the light source 8 for example by solder and wires or the like, not shown. The retaining ring 21 threads into the front housing 2 to retain the lens 3. The front housing 2 and back housing 6 are attached to one another about the body 1 by screws 7. The back housing 10 retains the diffuser 4 and o-ring 20 against the body 1. Source 8 is held in place to the back housing 6 by screws 9. Screw 11 is rotateably held in place on cover 10 by clip 12. Screw 11 further holds cover 10 in place against housing 6 over assembly 8.

The gauge set 900 further has a cap 13, spring 14, clutch adapter 15, clutch bottom disc 16, clutch top disc 17, nut 18 and hook 19. The nut 18 is threaded onto the hook 19. The spring 14, clutch adapter 15, clutch bottom disc 16, clutch top disc 17 are placed on the hook 19. The cap 13 is threaded onto the hook 19 to retain the 14, clutch adapter 15, clutch bottom disc 16, clutch top disc 17 in place between the nut 18 and cap 13. The spring 14 holds the clutch comprising the clutch adapter 15, clutch bottom disc 16, and clutch top disc 17 in place and thus the hook 19 in a given rotational alignment with the body 1. The force of the spring 14 may be overcome by turning the hook 19 such that the clutch top disc 17 (held in rotational alignment with the hook 19 by the nut 18) and the clutch bottom disc (held in rotational alignment with the adapter 15 which is in turn held in rotational alignment with the body 1 by the front housing 2 and the back housing 6) move with respect to one another to a different rotational alignment. This allows the hook 19 to be selectively rotationally aligned with respect to the body 1 such that the manifold gauge set 900 can be rotationally positioned with respect to the hook 19 by an operator for improved viewing. The clutch provides selectable rotational alignment of the hook 19 and body 1. Other clutch mechanisms could be used. Other non-clutch mechanisms to provide selectable rotational alignment could be used.

The gauge set 900 has hose spuds 22 and blank hose spuds 23. Hose spuds 22 connect to cavity 103 while blank hose spuds 23 do not. The hose spuds 22, 23 are held in place to the body 1 by threads, not shown. The hose spuds 22 act as couplers for hoses, not shown. The particular hose spuds 22 used for a given application can vary as desired. Typically quick disconnect fittings such as those shown in the FIGS. will be used for applications involving R134A refrigerant and may be used for other applications. Blank hose spuds 23 are provided to receive hose ends opposite to the hose ends connected to the hose spuds 22 when the opposite hose ends are not in use. This makes storage of the hoses easier and limits the possibility that the opposite ends will be contaminated, for example, by dragging them on the ground.

The gauge set 900 further has poppets 24, o-ring seals 25, poppet restraint washers 26, poppet holder sleeves 27, valve holders 28, calibration ring assembly 39, handles 29, handle washers 30, handle attaching screws 31, low side decal 35 and high side decal 36. the decals 35, 36 indicated open and close directions for the handles 29. These components are assembled together with the manifold body 1 to provide valves to control fluid communication between the hose spuds 22.

The gauge set 900 further has porous discs 34, high side pressure gauge 37, low side pressure gauge 38, and o-rings 40. These components are assembled to allow fluid communication between the gauges 37, 38 and the cavity 103 through the porous disc 34 to allow pressure readings to be displayed. The gauges 37, 38 may take different forms, for example, mechanical with an analog display, as shown, or electronic with a digital display.

The clutch bottom disc 16 and the clutch top disc 17 have corresponding teeth 44 to increase the friction between the discs 16, 17, while allowing release of the clutch and selection of the rotation position.

It is recognized that all fluid connections forming part of a fluid path through the gauge set 900 are sealed fluid connections. Such connections may be made in any matter which is sufficient to withstand pressures to be encountered when in use in a desired application. Such connections may for example be threaded, may for example use seals such as o-ring seals, and may for example use Teflon tape or the like, not shown.

The light source 8 as shown in the FIGS. is a circuit board assembly 8 comprising a circuit board 50 and LEDs 52. The LEDs 52 as shown are standard round package LEDs. Other package configurations could be used, such as for example surface mount LEDs. The circuit board assembly 8 also has a battery holder 54 for a flat coin-type battery, not shown. This type of battery will usually be sufficient for this application as the light source 8 is used intermittently for short periods. Other batteries could be used with consequent modification to the shape of the battery holder 54 and other components of the gauge set 900. The circuit board assembly 8 may also have a control circuit such as those described previously to interpret input from the switch 5 and control the LEDs 52 accordingly. The control circuit may for example also include such features as a debounce circuit and a timer shut-off to extend battery life. As mentioned previously, the LEDs 52 may be of different types, for example white light and light for causing visible fluorescence of additives sometimes used in refrigeration systems. One LED 52 or more LEDs 52 may be used as desired for a particular application.

The manifold body 1 has a longitudinal cavity 103 between the high side port 22a and low side port 22b. In the example shown in the FIGS. the cavity 103 (see in particular FIG. 13) extends from one end 56 of the body 1 to an opposing end 58 and is enclosed by valves 60, 62. Perpendicular to the longitudinal cavity 1 is a bore 64 through the body 1. The bore provides a first aperture 66 to the cavity 103 and an opposing second aperture 68 (see FIG. 12 in particular) to the cavity 103. The respective apertures 66 are enclosed by the front housing 2, lens 3 and retaining ring 21 and by the back housing 6, diffuser 4 and o-ring seal 6. The back housing 6 has an aperture 70 (see FIG. 14 in particular) through which LEDs 52 illuminate the diffuser 4 and thus the aperture 68 and cavity 103. Thus, a viewing window is provided by the lens 3 through the aperture 66 to the cavity 103 and the cavity 103 is backlit through the diffuser 4 by the light source 8 for viewing through the viewing window. It is to be recognized that other cavity shapes and other quantities and placements of valves are possible.

The lens 3 may be dome shaped or otherwise provide magnification for enhanced viewing of the cavity 103 as described previously. Alternatively, the lens 3 may simply be a flat lens as ordinarily used in sight glass windows to enclose the manifold cavity 103 while allowing viewing of the cavity 103. Other shapes may be used for the lens 103 as described previously for other embodiments.

Other techniques may be used to provide a viewing window and backlight for the cavity 103. For example, it is not necessary to provide separate housing 2, 6. The viewing window and backlight could be directly attached, such as by providing threads about aperture 66, 68 to receive retaining ring 21 and to receive a corresponding retaining ring, not shown for a backlight assembly. As a further example, the second aperture could be of a smaller diameter than aperture 66 to retain a single LED directly illuminating the cavity 103.

Thus, alternate paths can be provided for illuminating the cavity 103. The LED package could provide a diffuser, if desired.

The cavity 103 could be illuminated by LEDs through an aperture out of line with the aperture 66. As described previously, the sight glass itself could be tubular, providing integrated viewing window and light transmissive window and thus not have an aperture into which lens are placed, but rather be viewed from one direction and backlit from an opposing direction. Alternatively, illumination could be from an alternative direction from the viewing direction which alternative direction provides illumination to the cavity 103 while viewing the cavity 103 from the viewing direction.

Typically valves in existing manifold gauge sets are flat faced poppets that close off a flow hole. As the valve is opened by turning a knob, the hole goes from closed to full open flow in about 1 turn of the knob or less. Sometimes even only ½ turn. There is very little or no control of the refrigerant flow. The valve is basically on full or off. This type of valve or many other forms of valve can be used.

The valves 60, 62 provide graduated flow control. Also, the flow control can be calibrated. A tapered poppet 24 fits into a tapered portion 80 of the conduit 103 (see FIG. 13). The poppet 24 requires four full turns of the handle 29 to go from no flow to full flow. This provides a user with control of fluid flow through the cavity. The poppet 24 can be opened gradually instead of very quickly. More turns are required to get to full flow.

Numbers 82 are provided on the calibration ring 39 that will correspond with a given flow. The technician will become familiar with throttling refrigerant at for instance two full turns plus a number "3" 82 on the ring 39 as a desired flow. The technician needs to remember the number of rotations of the handle 39 before come to rest at a given number 82. The valves 60, 62 are multi-position valves as positions are available to progressively control fluid flow between full OFF and full ON positions. The numbers 82 represent rotational position indicators. Other rotational position indicators may be used.

As all components are subject to tolerances, no valve 60, 62 will turn off at exactly the same position of the handle 29. The calibration ring 39 can be moved with respect to the handle 29 to calibrate the valve 60, 62. The valve 60, 62 is turned off tight with no flow. The technician rotates the calibration ring 39, which has a friction fit on the handle 29, such that number "0" 82 lines up with a mark 84 on the body 1. Now the technician opens and closes the valve 60, 62 by rotating the handle 29 such that the calibration ring 39 will turn with the handle 29 because of the friction fit between the ring 39 and the knob 29. The valve 60, 62 is now calibrated such that the number "0" 82 on the calibration ring 39 indicates OFF.

The valve 60, 62 also has seals 25 on it that compresses during the last movement to provide a positive seal so the valve 60, 62 does not have to be closed hard enough to effect a metal to metal seal. In some embodiments the valve 60, 62 has been configured to make a positive seal during the last 0.025 inch of travel which was associated with about ¼ of a turn of the handle 29.

If the number "0" 82 is lined up when the valve 60, 62 is closed tight, as the handle 29 is turned to open the valve 60, 62, there will not be fluid flow for up to ¼ of a turn. The actual amount of a turn may vary with pressure as higher pressure will push past the rubber seal sooner than lower pressure. The technician may wish to turn the calibration ring 39 to correspond to when flow actually begins, instead of the full off position. Wherever the calibration ring 39 is set, the ring 39 will provide a consistent indication of flow for a given handle rotation which flow can be repeated for similarly calibrated valves 60, 62 in other manifolds or other device with which the valve 60, 62 is used in fluid connection with a refrigeration system.

Figure 15:
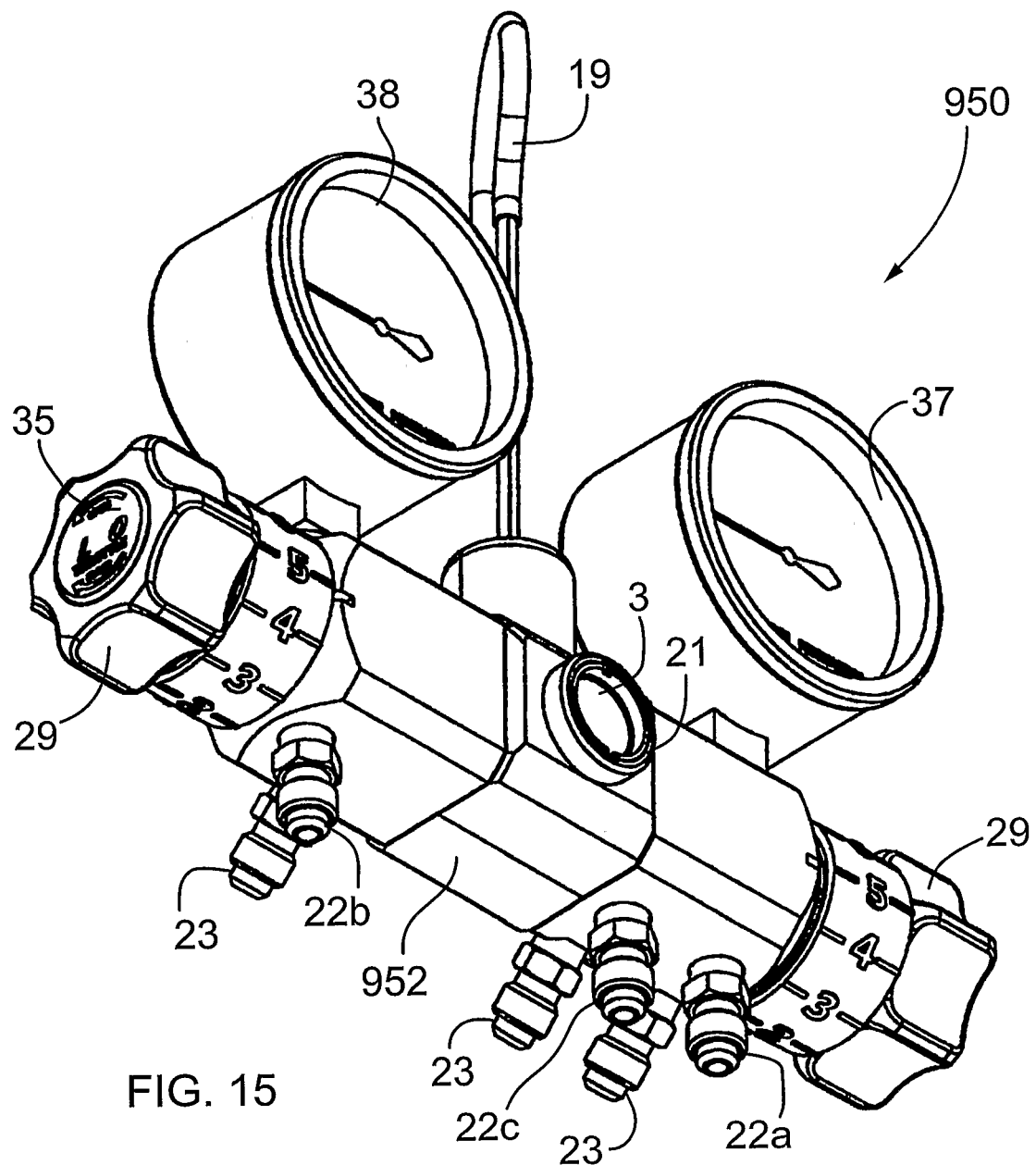
FIG. 15 is a perspective view from in front, below and to one side of a further alternate example embodiment of a manifold gauge set.
Figure 16:
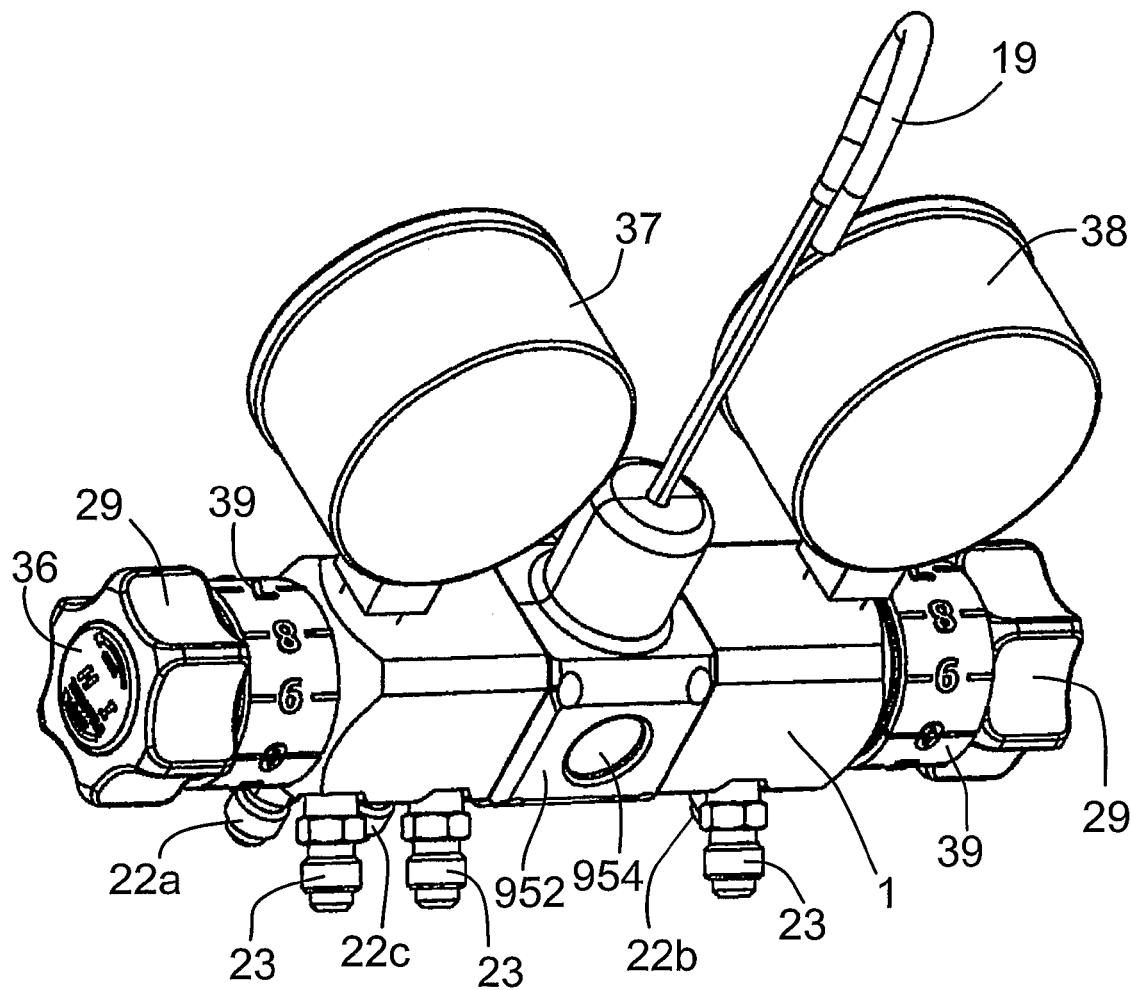
FIG. 16 is a perspective view from behind, above and to another side of the manifold gauge set of FIG. 15.
Figure 17:
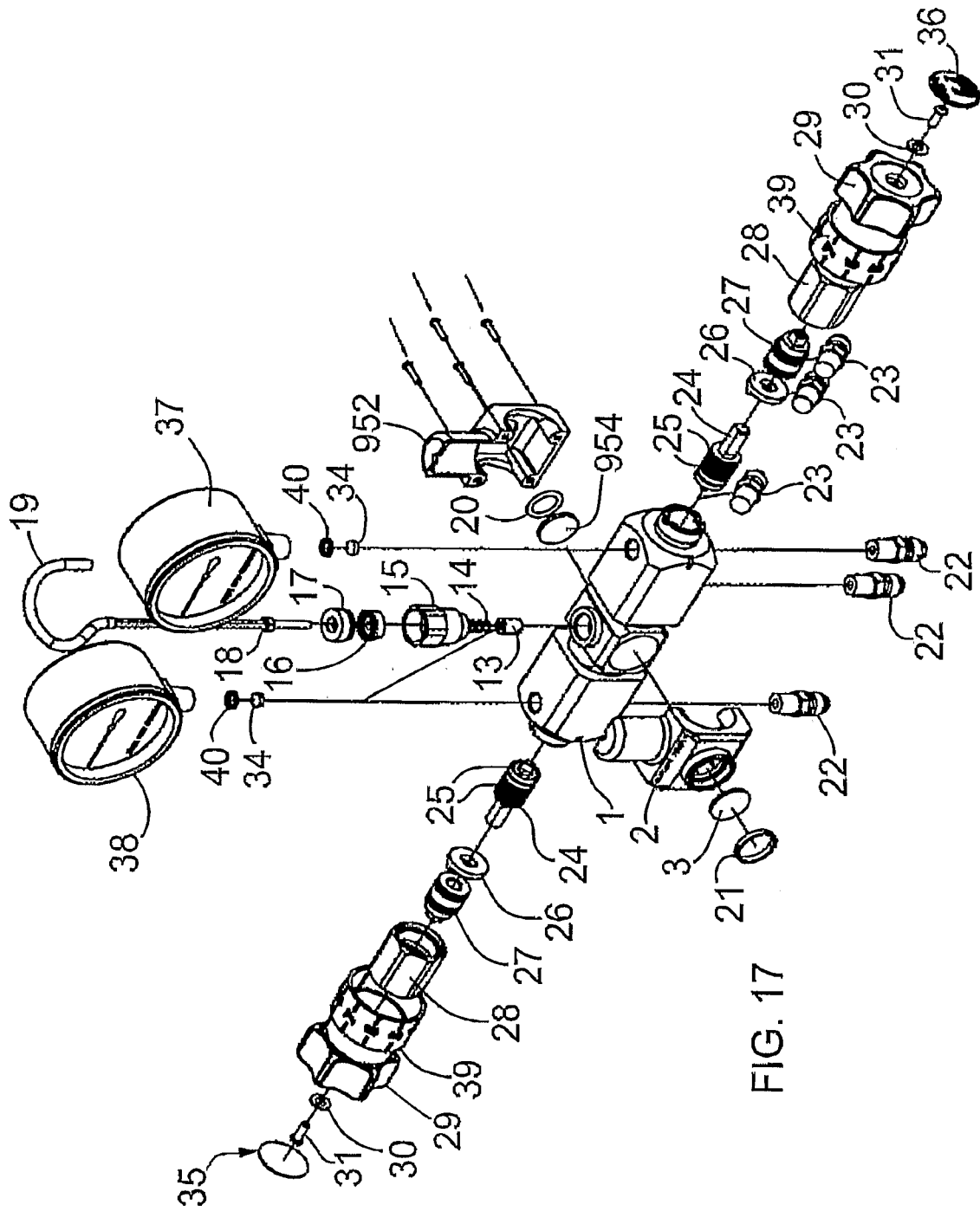
FIG. 17 is an exploded perspective view of the manifold gauge set of FIG. 15.

Referring to FIG. 15-17, a manifold gauge set 950 is similar to the gauge set 900. Parts with like reference numerals have similar structure and function. For simplicity, the description of such parts will not be repeated.

Back housing 952 replaces back housing 6, while lens 954 can replace diffuser 4. Passive backlight is provided to the cavity 103 through the lens 954 for the viewing window provided by lens 3 to the cavity 103. The lens 954 provides a rear viewing window if desired to be used as such with passive backlighting being provided through the lens 3. Illumination could be provided by ambient light. Alternatively, a separate light source, not shown, could be used to illuminate the cavity through one of lenses 954, 3 for viewing through the other lens 3, 954. Again, the illumination window could be provide out of line with the viewing window, if desired. A diffuser 4 could be utilized, if desired.

Figure 18:
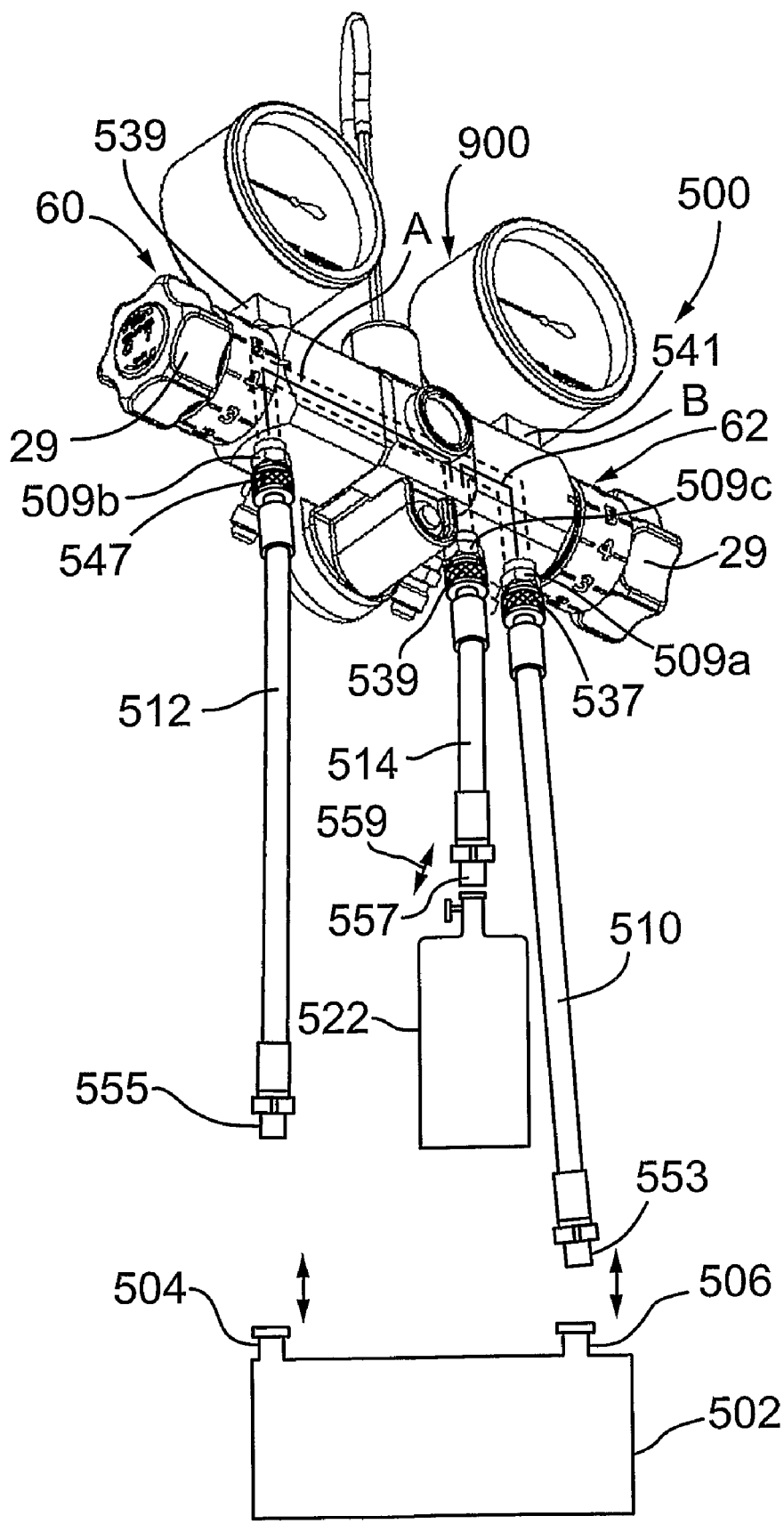
FIG. 18 is diagrammatic view of a conduit including a refrigeration system, manifold gauge set of FIGS. 9-11, charging station and connecting hoses in accordance with an example embodiment.

Referring to FIG. 18, a conduit 500 provides a sealed path for fluid connection to a refrigeration system 502. As shown in FIG. 18, the system 502 has a high pressure side port 504 and low pressure side port 506 providing access to the high pressure side and low pressure side, respectively, of the system 502. It is to be recognized that high pressure and low pressure in a refrigeration system 502 are relative terms. When in operation, low pressure is higher than ambient pressure surrounding the system 502, and high pressure is higher than low pressure.

Conduit 500 has a manifold gauge set 900. The set 900 has a high pressure side hose port 509a (coupler 22a) for connection to high pressure side hose 510, low pressure side hose port 509b (coupler 22b) for connection to low pressure side hose 512, charging hose port 509c (coupler 22c) for connection to charging hose 514, high pressure gauge 516, low pressure gauge 518, support 520 and charging station 522. The charging station 522 typically contains refrigerant for charging a refrigeration system and for conveying additives to a refrigeration system. For automotive air conditioning systems, the refrigerant is typically R12 or R134A; however, other refrigerants may be used for automotive air conditioning systems or other refrigeration systems, including for example $CO_2$. Additives may include for example lubricants and liquid dyes. The conduit 500 connects the charging station 522 and each of the other components of the conduit 500 to the system 502. The high pressure side hose 510 is connected to the high pressure side port 508 of the system 502. Similarly, the low pressure side hose 512 is connected to the low pressure side port 510, and the charging hose 514 is connected to the charging station 522.

Internally, the manifold gauge set 900 has a fluid path A from charging hose port 525 to low pressure side port 509b and a fluid path B from charging hose port 525 to high pressure side port 509a. The fluid paths A, B are controlled by high pressure valve 62 and low pressure valve 60, respectively. The valves 60, 62 have respective handles 29 extending from the manifold 900 to allow manual actuation of the valves 60, 62. Fluid path A also opens to low pressure gauge port 539 between valve 60 and port 509b. Fluid path B also opens to high pressure gauge port 541 between valve 62 and port 509a.

The charging hose port 525, high pressure side port 509a and low pressure side port 509b are typically quick disconnect fittings used in association with R134A refrigerant; however, the fittings may be R12 threaded male fittings or may be used in association with other refrigerants. This allows for connection of a corresponding female fitting for connection to a standard charging station. Many alternative forms of connections could be provided at the ports 525, 509a, 509b. Adapters, not shown. may be provided from fittings of one connection type to another type. Corresponding fittings 537, 539, 547 are provided in the hose 510, 512, 514.

The low pressure hose 512 and the high pressure hose 510 terminate in fitting 555, 553, such as for example R134A quick disconnect low side and high side fittings, respectively, for manual connection to the refrigeration system 502, or threaded R12 fittings. The charging hose 514 terminates in a fitting 557 for connection 559 to the charging station 522. In this case, the connection 559 is typically made by threading the fitting 557 with male threads into compatible female threads, not shown, in the charging station 522; however, other types of fittings may be used.

The manifold 900 valves 60, 62 could be opened with the charging port 525 capped to allow fluid flow from the high side 504 to the low side 506 to view the fluid flow through the viewing window.

Figure 19:
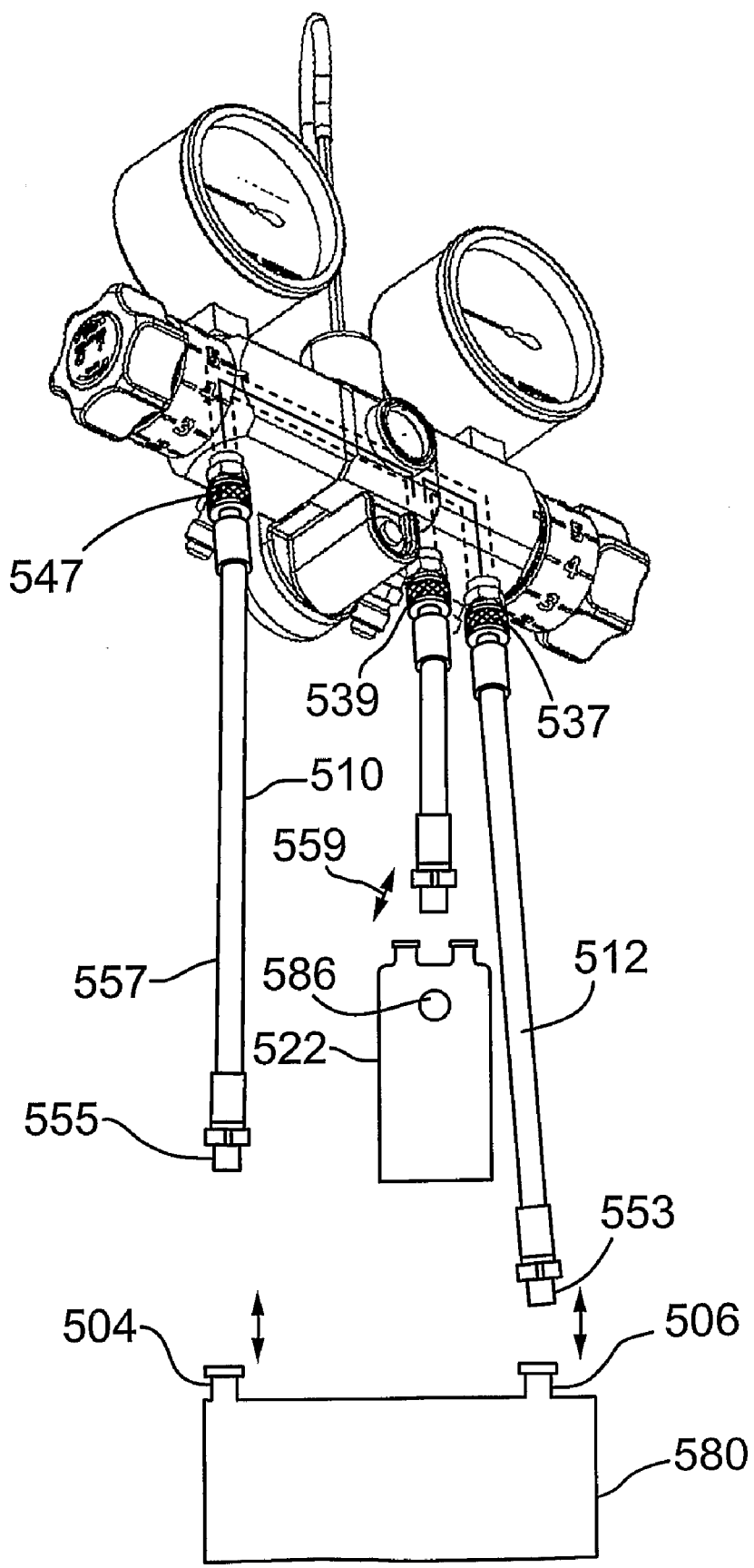
FIG. 19 is diagrammatic view of a conduit similar to that of FIG. 18 but with a refrigerant recovery machine in place of the charging station in accordance with another example embodiment.
Figure 20:
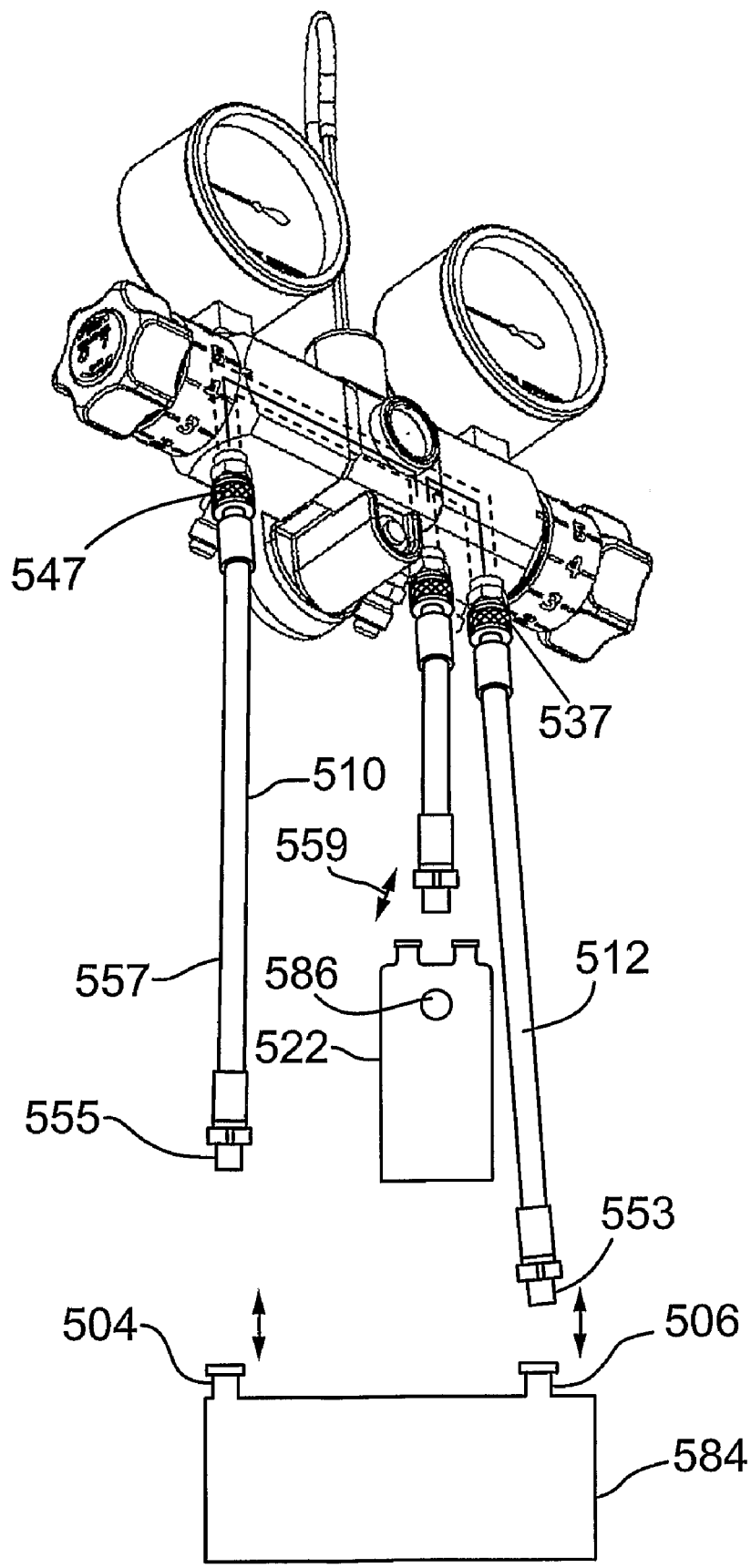
FIG. 20 is diagrammatic view of a conduit similar to that of FIG. 18 but with a refrigerant recovery and recycling machine in place of the charging station in accordance with a further example embodiment.

Referring to FIG. 19, the charging station 522 may be replaced with a recovery machine 580 for removing refrigerant from the refrigeration system 502 into a reservoir 582. Alternatively, the device may be a vacuum pump 580 for drawing a vacuum through the cavity 103. Referring to FIG. 20, alternatively, and as required in many jurisdictions, a recycling and recovery machine 584 may be used.

Referring to FIGS. 19 and 20, the recovery machine or vacuum pump 580 or recycling and recovery machine 584 may utilize a sight glass (the viewing window 586 of which is shown in the FIGS.) in the form described for use in association with the manifold gauge sets 900, 950 as the machines 580, 584 also contain cavities through which fluid flows. In most cases an active backlight with its own illumination source such as that in manifold gauge set 900 will be desirable as the rear of the machines 580, 584 may be difficult to access from the cavity for receiving external light. It is possible to provide out of line illumination to the cavity as described with respect to the embodiments in manifold gauge sets 900, 950.

Figure 21:
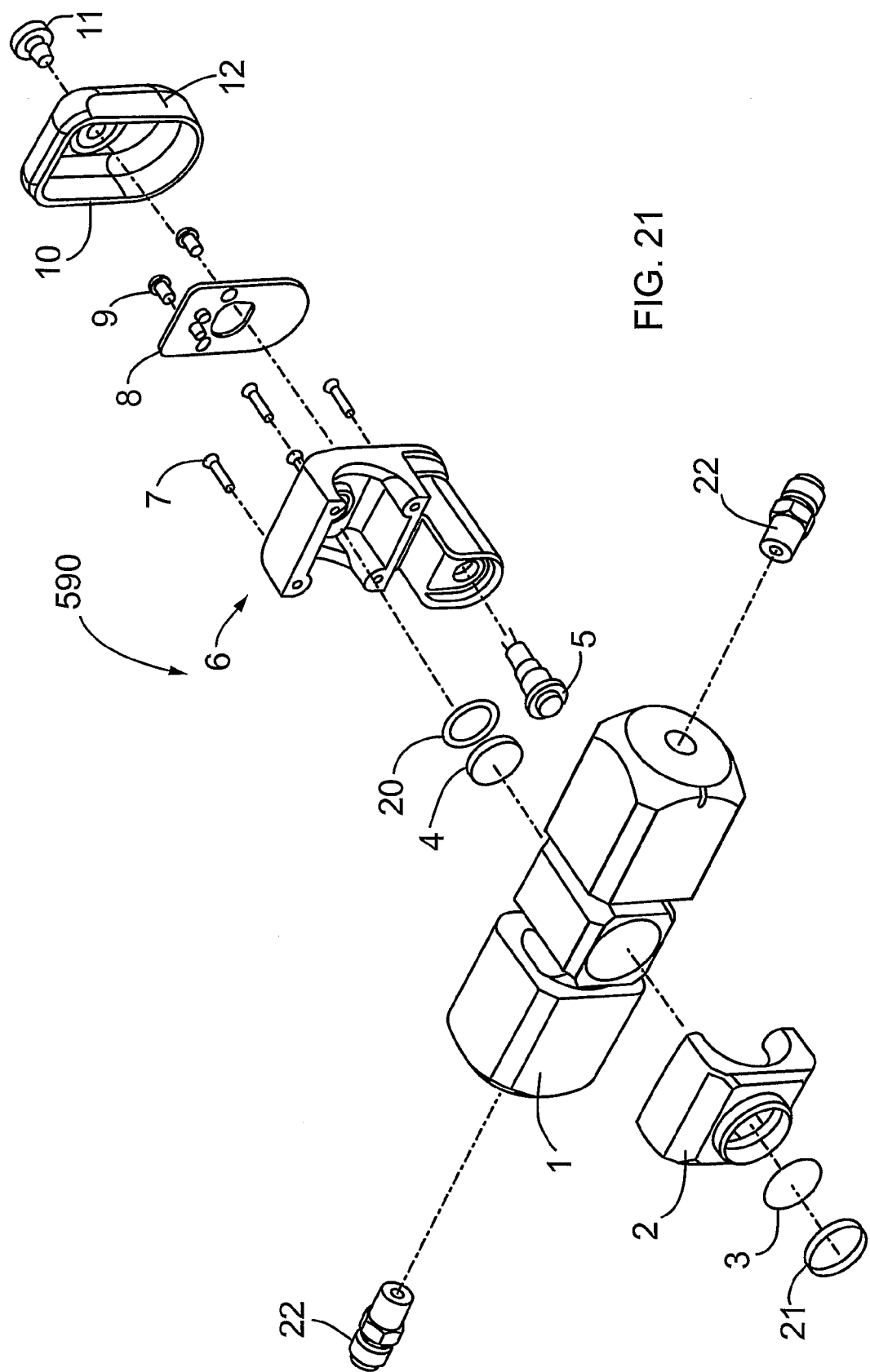
FIG. 21 is a perspective view of an inline sight glass in accordance with an example embodiment.

Referring to FIG. 21, standalone sight glass 590 incorporates many of the features of the manifold gauge set 900. Neither pressure gauges, valves nor a service port are provided; however, the sight glass 590 has an illuminated cavity 103 with a viewing window and light transmissive window and light source in the form of a backlight, and first and second ports 22 (similar to ports 22 of set 900) to the cavity for fluid connection to a refrigeration system. A standalone sight glass need not be longitudinally aligned as shown. Standalone as used herein means that the sight glass is not integrated with another device having a function other than to be a sight glass.

Figure 22:
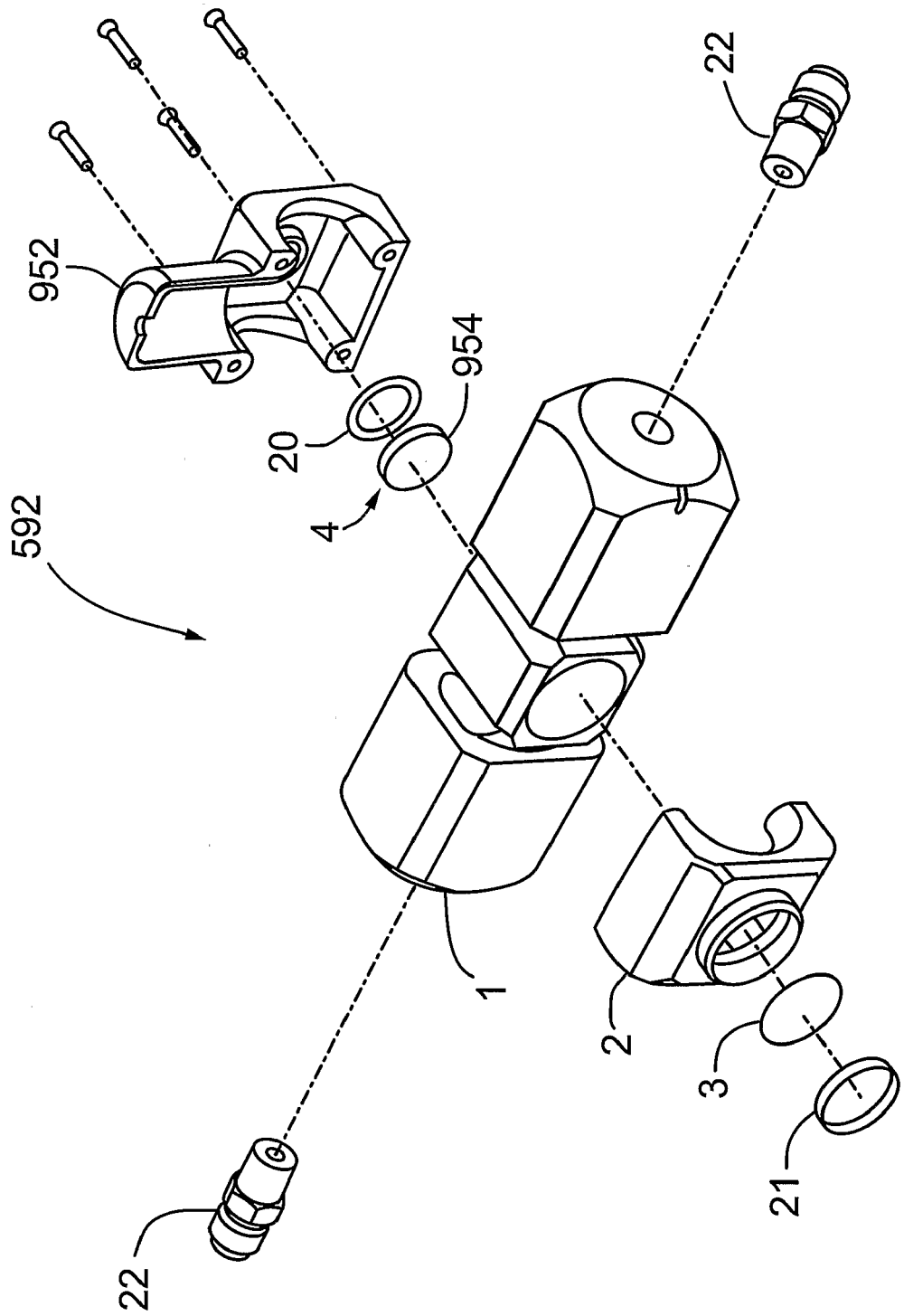
FIG. 22 is a perspective view of an alternate inline sight glass in accordance with another example embodiment.

Again, alternative versions of a standalone inline sight glass 590 can be provided. For example, referring to FIG. 22, a passive illuminated sight glass 592 may be utilized having some features of the gauge set 950. The structure and function thereof can be understood from the FIG. and the description provided for the active illumination sight glass 590 above in conjunction with the description of the manifold gauge set 950. Accordingly, additional description thereof will not be provided herein.

Figure 23:
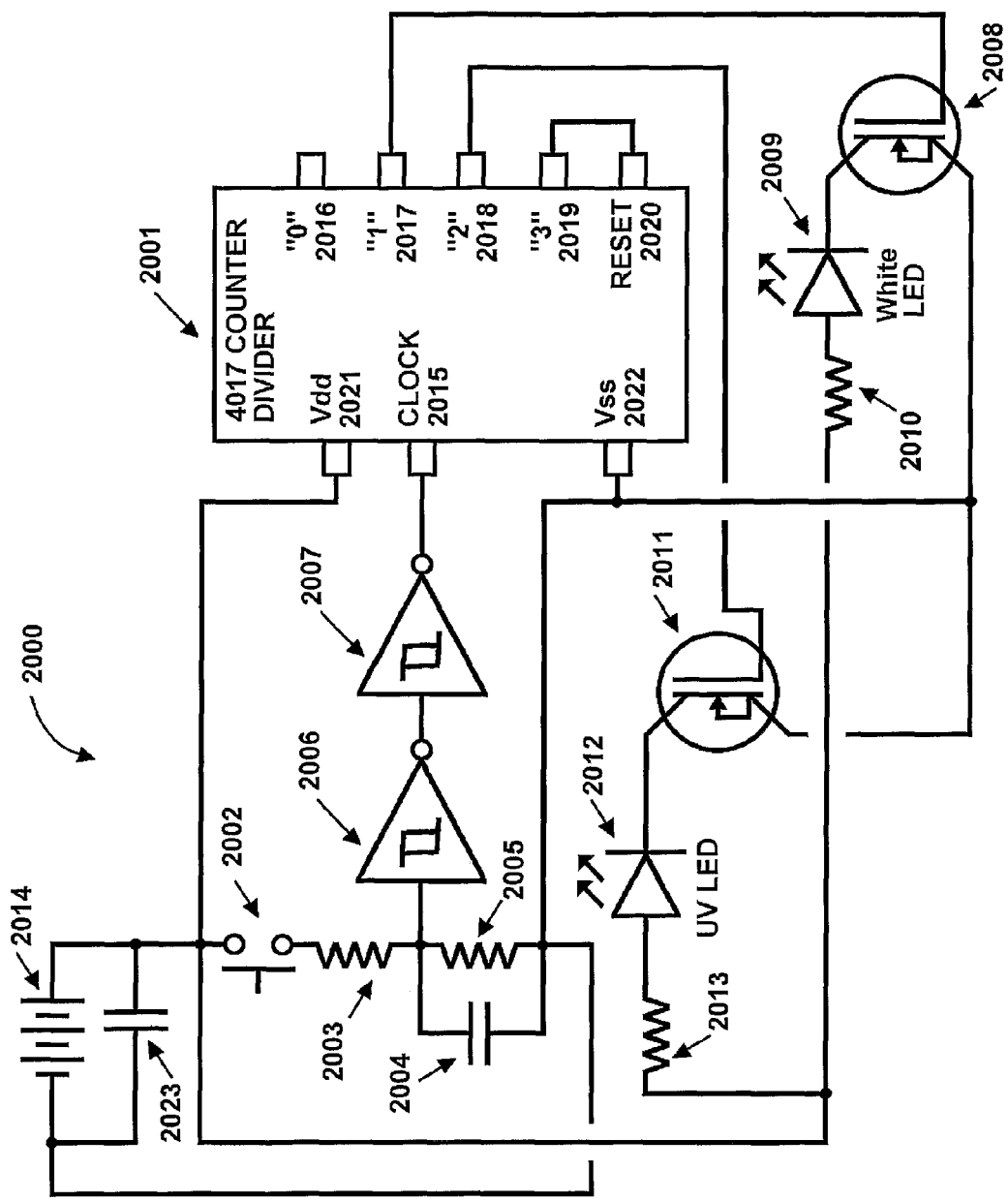
FIG. 23 is example circuitry for use in a light source for embodiments described herein.

Referring to FIG. 23, a circuit 2000 for a light source used in the present invention is shown. Shown as provided are a white LED 2009, a UV LED 2012, and a pushbutton 2002 used to switch on and off the LEDs 2009, 2012. The white LED is typically used for illumination to view the contents of a body cavity in a manifold gage set. The UV LED is typically used to cause fluorescence of any fluorescent material in the body cavity of a manifold gage set, such as refrigerant that is mixed with a lubricant having a fluorescent dye. A blue LED can be used in lieu of or in addition to the UV LED.

The pushbutton 2002 controls a 4017 counter divider 2001 to provide a sequence of operation of the LEDs 2009, 2012. A debounce circuit comprising a first Schmidt trigger inverter 2006, a second Schmidt trigger inverter 2007, a capacitor 2004, a charging resistor 2003 and a discharge resistor 2005 is provided to improve response of the 4017 counter divider 2001 to the pushbutton 2002. Without the debounce circuit, a control signal from the pushbutton 2002 may change unsteadily in response to pressing the pushbutton 2002 and cause the 4017 counter divider to change state more than once. The output of the second Schmidt trigger inverter 2007 controls the clock pin 2015 of the 4017 counter divider 2001. Other debounce circuits are known and can be used in lieu of the one shown. Alternatively, the light source circuit 2000 may be implemented without a debounce circuit if the pushbutton 2015 provides a signal that results in acceptable operation of the 4017 counter divider circuit 2001.

When the pushbutton 2002 is pressed, the capacitor 2004 is charged through the charging resistor 2003. The resistor 2003 and capacitor 2004 preferably have values resulting in a charging time constant of a few milliseconds. When the voltage across the capacitor 2004 exceeds the upper threshold of the first Schmidt trigger inverter 2006, the output of the first Schmidt trigger inverter 2006 changes from high to low. This causes the output of the second Schmidt trigger inverter 2007 to change from low to high.

When the pushbutton 2002 is released, the capacitor 2004 is discharged by the discharge resistor 2005. The discharge resistor 2005 must have a value sufficiently large compared to the value of the charging resistor 2003 for the voltage divider formed by these resistors 2003, 2005 to provide a voltage reliably exceeding the upper threshold of the first Schmidt trigger inverter 2006. The discharge resistor 2005 should have its value also resulting in a sufficiently short discharge time constant with the capacitor 2004, preferably approximately two tenths of a second or less. For clarity, power supply connections to the Schmidt trigger inverters 2006, 2007 are not shown.

Values found to work well are 470 kiloohms for the charging resistor 2003, 4.7 megohms for the discharge resistor 2005, and 0.01 microfarad for the capacitor 2004.

The Schmidt trigger inverters 2006, 2007 may be inverter sections of a 40106 integrated circuit. Alternatively, other Schmidt trigger inverters are available. Further alternatively, Scmidt trigger inverters can be formed from other components, such as some linear timer integrated circuits.

The 4017 counter divider 2001 is shown as being connected as a divide-by-three circuit. Only the Vdd pin 2021, Vss pin 2022, Clock pin 2015, output pin number zero 2016, output pin number 1 2017, output pin number 2 2018, output pin number 3 2019, and reset pin 2020 of the 4017 counter divider 2001 are shown. The output pin number zero 2016 is not shown as being used. The reset pin 2020 is connected to the number 3 pin 2019 to form a divide-by-three circuit.

When the signal received by the clock pin 2015 changes from low to high, the 4017 counter divider 2001 increments its state among the available output states zero through 9. When the output state reaches 3, the output pin number 3 2019 provides a high signal to the reset pin 2020 and causes the 4017 counter divider 2001 to immediately reset to output state zero. As a result, repeated pressing and releasing of the pushbutton 2002 causes the 4017 counter divider 2001 to cycle among the output states zero, 1 and 2. Respectively, one of the output pins number zero 2016, number 1 2017 and number 2 2018 to be high, one at a time.

Not shown is power on reset circuitry that may be provided so that the 4017 counter divider 2001 is forced to initialize in its number zero state when a battery 2014 is connected.

The number 1 pin is shown as controlling the white LED 2009 via a transistor 2008. The number 2 pin is shown as controlling the UV LED 2012 via a transistor 2011. Dropping resistors 2010, 2013 are preferably provided to limit the magnitude of the current that flows through the white LED 2009 and the UV LED 2012 respectively. The transistors 2008, 2011 are shown as being MOSFETs, although it is foreseeable that bipolar transistors can be used.

As a result, when the 4017 counter divider 2001 is in its zero state, neither the white LED 2009 nor the UV LED 2012 is on. Pressing the pushbutton 2002 then results in the white LED being on. Pressing the pushbutton 2002 again then results in the white LED 2009 turning off and the UV LED 2012 turning on. Pressing the pushbutton 2002 after that causes the 4017 counter divider 2001 to return to its zero state and both LEDs 2009, 2012 will both be off.

Alternative circuits are possible. For example, a programmable logic integrated circuit such as a microprocessor may be used in lieu of the 4017 counter divider 2001. A further variation of the circuit 2000 can have the LEDs 2009, 2012 controlled directly by the 4017 counter divider 2001 or alternative logic circuit rather than via the transistors 2008, 2011 if the LEDs 2009, 2012 provide sufficient output from the magnitude of the current that can be provided by such a logic circuit.

A battery 2014 is shown as being the power supply for the circuit 2000. A power supply bypass capacitor 2023 is shown as being connected in parallel with the battery 2014 to absorb noise resulting from switching of the circuit 2000. The Vdd pin 2021 and the Vss pin 2022 of the 4017 counter divider are connected to the positive and negative terminals respectively of the battery 2014.

As will be evident from the description and drawings provided herein it is possible to create embodiments of the invention with features and functions that provide easy and accurate inspection of liquid condition. For example, such embodiments can make it easier to see if there are bubbles present in the liquid stream and also if the cavity is full of liquid or only partially full of liquid or not filled with liquid.

It is to be recognized that the manifold gauge sets and other embodiments employing sight glasses and described herein can take many different forms. As one example, it is not necessary to have a body with the cavity configured longitudinally.

It is to be understood that the features and functions of one embodiment may be applied to other embodiments described herein. Not all combinations thereof have been described herein. It will be understood by those skilled in the art that this description is made with reference to the preferred embodiment and that it is possible to make other embodiments employing the principles of the invention which fall within its spirit and scope as defined by the following claims.

What is claimed is:

1. A device for use in servicing a refrigeration system, the device comprising:
    a body having a cavity,
    a viewing window for viewing contents of the cavity,
    a first hose connection port in fluid communication with the cavity and a second hose connection port in fluid communication with the cavity, the hose connection ports for forming respective fluid connections as part of a conduit in fluid connection with the refrigeration system, and
    a light source for illuminating the cavity.

2. The device of claim 1 further comprising a path through the body outside the hose connections ports, the path for allowing illumination of the cavity by the light source.

3. The device of claim 2 wherein the light source is mounted to the body.

4. The device of claim 3 wherein the path comprises an aperture through the body outside the viewing window, and the path comprises a light transmissive window enclosing the aperture.

5. The device of claim 1 wherein the light source comprises at least one LED.

6. The device of claim 5 wherein the light source comprises a plurality of LEDs,
    wherein at least one LED emits white light and at least one LED different from the white LED emits light for causing visible fluorescence of fluids utilized in refrigeration systems.

7. The device of claim 5 further comprising control circuitry for activating the white light at least one LED independently from the at least one LED for causing visible fluorescence.

8. The device of claim 1, wherein the light source is removable.

9. The device of claim 1, wherein the light source comprises a housing and connections for a battery to power the light source.

10. The device of claim 9 wherein the light source accepts power from an external power source to power the light source.

11. The device of claim 10, wherein the light source further comprises means to automatically prevent power from being consumed from the battery when external power is being provided.

12. A method of servicing a refrigeration system, the method comprising:
    forming respective fluid connections to a first hose connection port and to a second hose connection port as part of a conduit for fluid connection with the refrigeration system, the hose connection ports being part of a device having a body and the hose connection ports being in fluid communication with a cavity of the body, the body having a viewing window for viewing contents of the cavity and the body having a path through the body to the cavity outside the hose connection ports and the viewing window for viewing of the cavity,
    illuminating the cavity through the path, and
    viewing the cavity through the viewing window while the cavity is illuminated and contents from the refrigeration system are flowing through the cavity.

13. The method of claim 12 further comprising opening at least one valve between the hose connection ports to allow fluid in the conduit to flow between the first hose connection port and the second hose connection port through the cavity while the cavity is illuminated and the cavity is being viewed through the viewing window.

14. The method of claim 12 further comprising forming a fluid connection to a third hose connection port as part of the conduit for fluid connection with the refrigeration system.

15. The method of claim 14 further comprising opening at least one valve between the first and third hose connection port to allow fluid in the conduit to flow between the first hose connection port and the third hose connection port through the cavity while the cavity is illuminated and the cavity is being viewed through the viewing window.

16. The method of claim 14 further comprising opening at least one valve between the second and third hose connection port to allow fluid in the conduit to flow between the second hose connection port and the third hose connection port through the cavity while the cavity is illuminated and the cavity is being viewed through the viewing window.

17. The method of claim 14 further comprising opening at least two valves, a first valve between the first and third hose connection port to allow fluid in the conduit to flow between the first hose connection port and the third hose connection port through the cavity, and a second valve between the second and third hose connection port to allow fluid in the conduit to flow between the second hose connection port and the third hose connection port through the cavity while the path is illuminated and the cavity is being viewed through the viewing window.

18. The method of claim 12 further comprising altering the appearance of the cavity through the viewing window when liquid is present within the cavity as compared to when liquid is absent from the cavity.

19. The method of claim 12 wherein illuminating the cavity comprises providing a light transmissive window as the path into the cavity through the body outside the hose connection ports and the viewing window.

20. The method of claim 12 wherein illuminating the cavity comprises activating a light source attached to the device such that the light source illuminates the cavity through the light transmissive window.

21. The method of claim 12 wherein illuminating the cavity comprises illuminating the cavity from opposite the viewing window such that the cavity is backlit with respect to the viewing window.

22. A manifold gauge set for use in servicing a refrigeration system, the manifold gauge set comprising:
    a body having a cavity,
    a viewing window for viewing contents of the cavity,
    at least three hose connection ports in fluid communication with the cavity, at least two valves for controlling fluid communication between the hose connection ports and the cavity,
    two pressure gauges, one gauge associated with a one of the hose connection ports and another gauge associated with another one of the hose connection ports, the gauge for reading and displaying the pressure at its associated hose connection port, and
    a path through the body outside the hose connection ports and the viewing window, the path for allowing illumination of the cavity.

23. A manifold gauge set for use in servicing a refrigeration system, the manifold gauge set comprising:
    a body having a cavity,
    at least three hose connection ports, each post in fluid communication with the cavity, and at least two valves for controlling fluid communication between the ports and the cavity, two pressure gauge, one gauge associated with a one of the hose connection ports and another gauge associated with another one of the hose connection ports, the gauge for reading and displaying the pressure at its associated hose connection port,
    at least one valve being a multi-position rotational valve allowing control over the flow of fluid through the cavity by rotation of a handle of the valve, and
    a ring associated the handle of each multi-position valve, the ring comprising position indicators to indicate rotational position of the handle.

24. A manifold gauge set for use in servicing a refrigeration system, the manifold gauge set comprising:
    a body having a cavity,
    at least three hose connection ports, each post in fluid communication with the cavity, and at least two valves for controlling fluid communication between the ports and the cavity,
    two pressure gauge, one gauge associated with a one of the hose connection ports and another gauge associated with another one of the hose connection ports, the gauge for reading and displaying the pressure at its associated hose connection port, and
    a liquid presence indicator for indicating the presence of liquid in the cavity.

\* \* \* \* \*